(12) United States Patent  
Stone et al.

(10) Patent No.: US 12,161,392 B2
(45) Date of Patent: *Dec. 10, 2024

(54) SYSTEM FOR INDUCING DESIRABLE TEMPERATURE EFFECTS ON BODY TISSUE

(71) Applicant: Boston Scientific Scimed, Inc., Maple Grove, MN (US)

(72) Inventors: Corbett W. Stone, San Diego, CA (US); Michael F. Hoey, Shoreview, MA (US); Arthur G. Blanck, Ramona, CA (US); Len Briggs, Carlsbad, CA (US); Mike Perry, Los Altos, CA (US); Rolfe Tyson Gustus, San Diego, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 903 days.

This patent is subject to a terminal disclaimer.

(21) Appl. No.: 16/524,359

(22) Filed: Jul. 29, 2019

(65) Prior Publication Data

US 2020/0000519 A1 Jan. 2, 2020

Related U.S. Application Data

(63) Continuation of application No. 13/385,555, filed on Feb. 24, 2012, now Pat. No. 10,413,356, which is a
(Continued)

(51) Int. Cl.
| | |
|---|---|
| *A61B 18/14* | (2006.01) |
| *A61B 18/00* | (2006.01) |
| *A61F 7/12* | (2006.01) |

(52) U.S. Cl.
CPC ............ *A61B 18/1492* (2013.01); *A61F 7/12* (2013.01); *A61F 7/123* (2013.01);
(Continued)

(58) Field of Classification Search
CPC ........ A61F 7/12; A61F 7/123; A61F 2007/12; A61F 2007/123; A61B 18/14;
(Continued)

(56) References Cited

U.S. PATENT DOCUMENTS

| | | |
|---|---|---|
| 164,184 A | 6/1875 | Kiddee |
| 1,167,014 A | 1/1916 | O'Brien |

(Continued)

FOREIGN PATENT DOCUMENTS

| | | |
|---|---|---|
| CA | 2384866 A1 | 4/2001 |
| CN | 1015583323 A | 11/2009 |

(Continued)

OTHER PUBLICATIONS

U.S. Pat. No. 8,398,630 B2, Mar. 2013, Demarais et al. (withdrawn).

(Continued)

*Primary Examiner* — Joseph A Stoklosa
*Assistant Examiner* — Adam J Avigan
(74) *Attorney, Agent, or Firm* — Seager, Tufte & Wickhem, LLP

(57) ABSTRACT

A catheter and catheter system may be used to treat disease tissue by gentle heating in combination with gentle or standard dilation. An elongate flexible catheter body with a radially expandable balloon having a plurality of electrodes engage tissue including diseased tissue when the structure expands.

5 Claims, 12 Drawing Sheets

Related U.S. Application Data continuation of application No. 11/975,383, filed on Oct. 18, 2007, now Pat. No. 9,125,667.

(60) Provisional application No. 60/976,733, filed on Oct. 1, 2007, provisional application No. 60/921,973, filed on Apr. 4, 2007, provisional application No. 60/852,787, filed on Oct. 18, 2006.

(52) U.S. Cl.
CPC ........... *A61B 2018/00214* (2013.01); *A61B 2018/0022* (2013.01); *A61B 2018/00702* (2013.01); *A61B 2018/00875* (2013.01); *A61F 2007/126* (2013.01)

(58) Field of Classification Search
CPC ............ A61B 18/12; A61B 18/1492; A61B 2018/0022; A61B 2018/00345; A61B 2018/00398; A61B 2018/0041; A61B 2018/12; A61B 2018/14; A61B 2018/1405; A61B 2018/1465
See application file for complete search history.

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin-Uddin |
| 3,952,747 A | 4/1976 | Kimmell, Jr. |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke |
| 5,071,424 A | 12/1991 | Reger |
| 5,074,871 A | 12/1991 | Groshong |
| 5,098,429 A | 3/1992 | Sterzer |
| 5,098,431 A | 3/1992 | Rydell |
| 5,102,402 A | 4/1992 | Dror et al. |
| RE33,925 E | 5/1992 | Bales et al. |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,151 A | 10/1992 | Imran |
| 5,156,610 A | 10/1992 | Reger |
| 5,158,564 A | 10/1992 | Schnepp-Pesch et al. |
| 5,170,802 A | 12/1992 | Mehra |
| 5,178,620 A | 1/1993 | Eggers et al. |
| 5,178,625 A | 1/1993 | Groshong |
| 5,190,540 A | 3/1993 | Lee |
| 5,191,883 A | 3/1993 | Lennox et al. |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg |
| 5,254,098 A | 10/1993 | Ulrich et al. |
| 5,255,679 A | 10/1993 | Imran |
| 5,263,493 A | 11/1993 | Avitall |
| 5,267,954 A | 12/1993 | Nita |
| 5,277,201 A | 1/1994 | Stern |
| 5,282,484 A | 2/1994 | Reger |
| 5,286,254 A | 2/1994 | Shapland et al. |
| 5,295,484 A | 3/1994 | Marcus et al. |
| 5,297,564 A | 3/1994 | Love |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,342,357 A * | 8/1994 | Nardella ............ A61B 18/1482 606/50 |
| 5,344,395 A | 9/1994 | Whalen et al. |
| 5,345,936 A | 9/1994 | Pomeranz et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita |
| 5,380,274 A | 1/1995 | Nita |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins |
| 5,403,311 A | 4/1995 | Abele et al. |
| 5,405,318 A | 4/1995 | Nita |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins |
| 5,447,509 A | 9/1995 | Mills et al. |
| 5,451,207 A | 9/1995 | Yock |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek |
| 5,498,261 A | 3/1996 | Strul |
| 5,499,981 A * | 3/1996 | Kordis ............ A61N 1/056 606/41 |
| 5,505,201 A | 4/1996 | Grill, Jr. et al. |
| 5,505,730 A | 4/1996 | Edwards |

(56) References Cited

U.S. PATENT DOCUMENTS

| | | |
|---|---|---|
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,132 A | 8/1996 | Fagan et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg et al. |
| 5,688,266 A | 11/1997 | Edwards et al. |
| 5,693,015 A | 12/1997 | Walker et al. |
| 5,693,029 A | 12/1997 | Leonhardt |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,792,105 A | 8/1998 | Lin et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory |
| 5,823,956 A | 10/1998 | Roth et al. |
| 5,827,203 A | 10/1998 | Nita |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine |
| 5,868,736 A | 2/1999 | Swanson et al. |
| 5,869,127 A | 2/1999 | Zhong |
| 5,871,483 A | 2/1999 | Jackson et al. |
| 5,871,524 A | 2/1999 | Knowlton |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell |
| 5,904,697 A | 5/1999 | Gifford, III et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream |
| 5,957,969 A | 9/1999 | Warner et al. |
| 5,961,513 A | 10/1999 | Swanson et al. |
| 5,964,757 A | 10/1999 | Ponzi |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |

(56) References Cited

U.S. PATENT DOCUMENTS

| | | |
|---|---|---|
| 6,004,269 A | 12/1999 | Crowley et al. |
| 6,004,316 A | 12/1999 | Laufer |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,019,757 A | 2/2000 | Scheldrup |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky |
| 6,033,357 A | 3/2000 | Ciezki et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,083,159 A | 7/2000 | Driscoll, Jr. et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals, Jr. et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,216,704 B1 | 4/2001 | Ingle et al. |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |

(56) References Cited

U.S. PATENT DOCUMENTS

| | | |
|---|---|---|
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,089 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,274 B1 | 2/2003 | Rosenthal et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,061 B2 | 8/2003 | Vantassel et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |

(56) References Cited

U.S. PATENT DOCUMENTS

| | | |
|---|---|---|
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Dscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Jais et al. |
| 6,837,888 B2 | 1/2005 | Ciarrocca et al. |
| 6,845,267 B2 | 1/2005 | Harrison et al. |
| 6,847,848 B2 | 1/2005 | Sterzer et al. |
| 6,849,073 B2 | 2/2005 | Hoey et al. |
| 6,849,075 B2 | 2/2005 | Bertolero et al. |
| 6,853,123 B1 | 2/2005 | Nattermann et al. |
| 6,853,425 B2 | 2/2005 | Kim et al. |
| 6,855,143 B2 | 2/2005 | Davison et al. |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | Lafontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,958,075 B2 | 10/2005 | Mon et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,008,667 B2 | 3/2006 | Chudzik et al. |
| 7,011,508 B2 | 3/2006 | Lum |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Pukas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buyesse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,160,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |

(56) References Cited

U.S. PATENT DOCUMENTS

| | | |
|---|---|---|
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Scachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,528,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Cassells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |

(56) References Cited

U.S. PATENT DOCUMENTS

| | | |
|---|---|---|
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,195 B2 | 6/2010 | Kakutani |
| 7,744,594 B2 | 6/2010 | Yamazaki et al. |
| 7,753,907 B2 | 7/2010 | Dimatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner et al. |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Vegesna et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | Lafontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Seigel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |

(56) References Cited

U.S. PATENT DOCUMENTS

| | | |
|---|---|---|
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2001/0051774 A1 | 12/2001 | Littrup et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062123 A1 | 5/2002 | Mcclurken et al. |
| 2002/0062146 A1 | 5/2002 | Makower et al. |
| 2002/0065542 A1 | 5/2002 | Lax et al. |
| 2002/0072686 A1 | 6/2002 | Hoey et al. |
| 2002/0077592 A1 | 6/2002 | Barry |
| 2002/0082552 A1 | 6/2002 | Ding et al. |
| 2002/0087151 A1 | 7/2002 | Mody et al. |
| 2002/0087156 A1 | 7/2002 | Maguire et al. |
| 2002/0091381 A1 | 7/2002 | Edwards |
| 2002/0095197 A1 | 7/2002 | Lardo et al. |
| 2002/0107511 A1 | 8/2002 | Jais et al. |
| 2002/0107536 A1 | 8/2002 | Hussein |
| 2002/0143324 A1 | 10/2002 | Edwards |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0004510 A1 | 1/2003 | Wham et al. |
| 2003/0028114 A1 | 2/2003 | Casscells, III et al. |
| 2003/0050635 A1 | 3/2003 | Truckai et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0069619 A1 | 4/2003 | Fenn et al. |
| 2003/0088189 A1 | 5/2003 | Tu et al. |
| 2003/0092995 A1 | 5/2003 | Thompson |
| 2003/0114791 A1 | 6/2003 | Rosenthal et al. |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0212394 A1 | 11/2003 | Pearson et al. |
| 2003/0223639 A1 | 12/2003 | Shlain et al. |
| 2003/0229340 A1 | 12/2003 | Sherry et al. |
| 2003/0229384 A1 | 12/2003 | Mon |
| 2003/0233099 A1* | 12/2003 | Danaek .............. A61B 18/1477 606/113 |
| 2004/0006333 A1 | 1/2004 | Arnold et al. |
| 2004/0006359 A1 | 1/2004 | Laguna |
| 2004/0010118 A1 | 1/2004 | Vernet et al. |
| 2004/0019348 A1 | 1/2004 | Stevens et al. |
| 2004/0024371 A1 | 2/2004 | Plicchi et al. |
| 2004/0039429 A1* | 2/2004 | Daniel .............. A61B 18/1477 607/100 |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0111016 A1 | 6/2004 | Casscells, III et al. |
| 2004/0117032 A1 | 6/2004 | Roth |
| 2004/0122421 A1 | 6/2004 | Wood |
| 2004/0147915 A1 | 7/2004 | Hasebe |
| 2004/0162555 A1 | 8/2004 | Farley et al. |
| 2004/0167506 A1 | 8/2004 | Chen |
| 2004/0181165 A1 | 9/2004 | Hoey et al. |
| 2004/0186356 A1 | 9/2004 | O'Malley et al. |
| 2004/0186468 A1 | 9/2004 | Edwards |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0010208 A1 | 1/2005 | Winston et al. |
| 2005/0015125 A1 | 1/2005 | Mioduski et al. |
| 2005/0033136 A1 | 2/2005 | Govari et al. |
| 2005/0080374 A1 | 4/2005 | Esch et al. |
| 2005/0090820 A1 | 4/2005 | Cornelius et al. |
| 2005/0096647 A1* | 5/2005 | Steinke .............. A61B 18/1492 606/41 |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward et al. |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0283195 A1 | 12/2005 | Pastore et al. |
| 2006/0004323 A1 | 1/2006 | Chang et al. |
| 2006/0018949 A1 | 1/2006 | Ammon et al. |
| 2006/0024564 A1 | 2/2006 | Manclaw et al. |
| 2006/0025765 A1 | 2/2006 | Landman et al. |

(56) References Cited

U.S. PATENT DOCUMENTS

| | | |
|---|---|---|
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1* | 4/2006 | Carmel .............. A61B 18/1492 606/41 |
| 2006/0095096 A1 | 5/2006 | Debenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0149166 A1 | 7/2006 | Zvuloni |
| 2006/0167106 A1 | 7/2006 | Zhang et al. |
| 2006/0167498 A1 | 7/2006 | Dilorenzo |
| 2006/0171895 A1 | 8/2006 | Bucay-Couto |
| 2006/0184060 A1 | 8/2006 | Belalcazar et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0235286 A1 | 10/2006 | Stone et al. |
| 2006/0239921 A1 | 10/2006 | Mangat et al. |
| 2006/0240070 A1 | 10/2006 | Cromack et al. |
| 2006/0246143 A1 | 11/2006 | Ege |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0280858 A1 | 12/2006 | Kokish |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0078498 A1 | 4/2007 | Rezai et al. |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0197891 A1 | 8/2007 | Shachar et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw et al. |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | Dilorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0074828 A1 | 3/2009 | Alexis et al. |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Williams et al. |
| 2009/0216317 A1 | 8/2009 | Cromack et al. |

(56) References Cited

U.S. PATENT DOCUMENTS

| | | |
|---|---|---|
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0312615 A1* | 12/2009 | Caduff ............... A61B 5/0531 600/347 |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0125239 A1 | 5/2010 | Perry et al. |
| 2010/0125268 A1 | 5/2010 | Gustus et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0248927 A1 | 9/2010 | Arashi et al. |
| 2010/0249604 A1 | 9/2010 | Hastings et al. |
| 2010/0249702 A1 | 9/2010 | Magana et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | Mccarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | Mcdaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118598 A1 | 5/2011 | Gertner |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178403 A1 | 7/2011 | Weng et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Naga et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Naga et al. |
| 2012/0136349 A1 | 5/2012 | Hastings |
| 2012/0136350 A1 | 5/2012 | Goshgarian et al. |
| 2012/0136417 A1 | 5/2012 | Mcmullin et al. |
| 2012/0136418 A1 | 5/2012 | Mcmullin et al. |
| 2012/0143181 A1 | 6/2012 | Demarais et al. |
| 2012/0143293 A1 | 6/2012 | Zarins et al. |
| 2012/0143294 A1 | 6/2012 | Clark et al. |
| 2012/0150267 A1 | 6/2012 | Sweeney et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |

(56) References Cited

U.S. PATENT DOCUMENTS

| | | |
|---|---|---|
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Vascular |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister et al. |
| 2013/0172880 A1 | 7/2013 | Willard |
| 2013/0172881 A1 | 7/2013 | Hill et al. |

FOREIGN PATENT DOCUMENTS

| | | |
|---|---|---|
| CN | 102271607 A1 | 12/2011 |
| DE | 10038737 A1 | 2/2002 |
| DE | 102005041601 A1 | 4/2007 |
| DE | 102008048616 A1 | 4/2010 |
| EP | 0558297 A2 | 9/1993 |
| EP | 0634910 A1 | 1/1995 |
| EP | 0647435 A1 | 4/1995 |
| EP | 0866675 A1 | 9/1998 |
| EP | 0868884 A2 | 10/1998 |
| EP | 1005838 A1 | 6/2000 |
| EP | 1053720 A1 | 11/2000 |
| EP | 1064886 A1 | 1/2001 |
| EP | 1180004 A1 | 2/2002 |
| EP | 1181895 A2 | 2/2002 |
| EP | 1264613 A1 | 12/2002 |
| EP | 1286625 A1 | 3/2003 |
| EP | 1297795 A1 | 4/2003 |
| EP | 1332724 A1 | 8/2003 |
| EP | 1433448 A1 | 6/2004 |
| EP | 1442719 A1 | 8/2004 |
| EP | 1547537 A1 | 6/2005 |
| EP | 1634542 A1 | 3/2006 |
| EP | 1698296 A1 | 9/2006 |
| EP | 1709922 A1 | 10/2006 |
| EP | 1715798 A1 | 11/2006 |
| EP | 1335677 B1 | 11/2007 |
| EP | 1874211 A2 | 1/2008 |
| EP | 1906853 A2 | 4/2008 |
| EP | 1946712 A1 | 7/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2092957 A1 | 8/2009 |
| EP | 2197533 A1 | 6/2010 |
| EP | 2208506 A1 | 7/2010 |
| EP | 1579889 B1 | 8/2010 |
| EP | 2241279 A1 | 10/2010 |
| EP | 2092957 B1 | 1/2011 |
| EP | 2329859 A1 | 6/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2313062 A | 11/1997 |
| GB | 2453601 A | 4/2009 |
| GB | 2456301 A | 7/2009 |
| JP | H07213621 A | 8/1995 |
| JP | H07313603 A | 12/1995 |
| JP | 2003510126 A | 3/2003 |
| WO | 9103207 A1 | 3/1991 |
| WO | 9117731 A1 | 11/1991 |
| WO | 9222239 A1 | 12/1992 |
| WO | 9320747 A1 | 10/1993 |
| WO | 9320770 A2 | 10/1993 |
| WO | 9418896 A1 | 9/1994 |
| WO | 9428809 A1 | 12/1994 |
| WO | 9501751 A1 | 1/1995 |
| WO | 9531142 A1 | 11/1995 |
| WO | 9634559 A1 | 11/1996 |
| WO | 9703604 A1 | 2/1997 |
| WO | 97017104 A1 | 5/1997 |
| WO | 9720510 A1 | 6/1997 |
| WO | 9732532 A1 | 9/1997 |
| WO | 9740760 A1 | 11/1997 |
| WO | 9745156 A2 | 12/1997 |
| WO | 9818393 A1 | 5/1998 |
| WO | 9829030 A1 | 7/1998 |
| WO | 9834565 A1 | 8/1998 |
| WO | 9835638 A1 | 8/1998 |
| WO | 9840023 A1 | 9/1998 |
| WO | 9858588 A1 | 12/1998 |
| WO | 9900060 A1 | 1/1999 |
| WO | 9916370 A1 | 4/1999 |
| WO | 9921608 A1 | 5/1999 |
| WO | 9934741 A1 | 7/1999 |
| WO | 9944522 A1 | 9/1999 |
| WO | 0001313 A1 | 1/2000 |
| WO | 0010475 A1 | 3/2000 |
| WO | 0047118 A1 | 8/2000 |
| WO | 0051513 A1 | 9/2000 |
| WO | 0059394 A1 | 10/2000 |
| WO | 0062727 A1 | 10/2000 |
| WO | 0064387 A1 | 11/2000 |
| WO | 0069376 A1 | 11/2000 |
| WO | 0072909 A1 | 12/2000 |
| WO | 0122897 A1 | 4/2001 |
| WO | 0137746 A1 | 5/2001 |
| WO | 0174255 A1 | 10/2001 |
| WO | 0187154 A1 | 11/2001 |
| WO | 0187172 A1 | 11/2001 |
| WO | 0195820 A1 | 12/2001 |
| WO | 0215807 A1 | 2/2002 |
| WO | 0208475 A1 | 4/2002 |
| WO | 0239915 A1 | 5/2002 |
| WO | 02058549 A1 | 8/2002 |
| WO | 02080766 A2 | 10/2002 |
| WO | 02087679 A2 | 11/2002 |
| WO | 02089686 A1 | 11/2002 |
| WO | 03026525 A1 | 4/2003 |
| WO | 03077781 A1 | 9/2003 |
| WO | 2004047659 A2 | 6/2004 |
| WO | 2004049976 A1 | 6/2004 |
| WO | 2004064606 A2 | 8/2004 |
| WO | 2004069300 A2 | 8/2004 |

(56) References Cited

FOREIGN PATENT DOCUMENTS

| | | | |
|---|---|---|---|
| WO | 2004076146 A2 | 9/2004 |
| WO | 2004098694 A1 | 11/2004 |
| WO | 2004100813 A2 | 11/2004 |
| WO | 2004105807 A2 | 12/2004 |
| WO | 2004110258 A2 | 12/2004 |
| WO | 2005007000 A1 | 1/2005 |
| WO | 2005037070 A2 | 4/2005 |
| WO | 2005041748 A2 | 5/2005 |
| WO | 2005074829 A1 | 8/2005 |
| WO | 2006041881 A2 | 4/2006 |
| WO | 2006105121 A2 | 10/2006 |
| WO | 2006116198 A2 | 11/2006 |
| WO | 2007011634 A1 | 1/2007 |
| WO | 2007014063 A2 | 2/2007 |
| WO | 20070478870 A2 | 4/2007 |
| WO | 2007113865 A1 | 10/2007 |
| WO | 2007135431 A1 | 11/2007 |
| WO | 2007146215 A2 | 12/2007 |
| WO | 2008003058 A2 | 1/2008 |
| WO | 2008009972 A2 | 1/2008 |
| WO | 2008010150 A2 | 1/2008 |
| WO | 2008014465 A2 | 1/2008 |
| WO | 2008036281 A2 | 3/2008 |
| WO | 2008049084 A2 | 4/2008 |
| WO | 2008061152 A2 | 5/2008 |
| WO | 2008102363 A2 | 8/2008 |
| WO | 2009036471 A1 | 3/2009 |
| WO | 2009082635 A1 | 7/2009 |
| WO | 2009088678 A1 | 7/2009 |
| WO | 2009113064 A2 | 9/2009 |
| WO | 2009121017 A1 | 10/2009 |
| WO | 2009137819 A1 | 11/2009 |
| WO | 2010042653 A1 | 4/2010 |
| WO | 2010048007 A1 | 4/2010 |
| WO | 2010056771 A1 | 5/2010 |
| WO | 2010057043 A1 | 5/2010 |
| WO | 2010067360 A2 | 6/2010 |
| WO | 2010070766 A1 | 6/2010 |
| WO | 2010099207 A1 | 9/2010 |
| WO | 2010102310 A2 | 9/2010 |
| WO | 2010120944 A1 | 10/2010 |
| WO | 2010134503 A1 | 11/2010 |
| WO | 2011005901 A2 | 1/2011 |
| WO | 2011053757 A1 | 5/2011 |
| WO | 2011053772 A1 | 5/2011 |
| WO | 2011055143 A2 | 5/2011 |
| WO | 2011060339 A1 | 5/2011 |
| WO | 2011091069 A1 | 7/2011 |
| WO | 2011126580 A2 | 10/2011 |
| WO | 2011130534 A2 | 10/2011 |
| WO | 2012019156 A1 | 2/2012 |
| WO | 2013049601 A2 | 4/2013 |

OTHER PUBLICATIONS

Brown et al; "Observations on the Shrink Temperature of Collagen and its Variations with Age and Disease," Ann Rheum Dis. 17(2): 196-208, Jun. 1, 1958.

Office Action issued in Chinese Patent Application No. 2011103923. X, dated May 22, 2012, 10 pages total.

Notice of the Reason for Refusal issued in Japanese Patent Application No. 2009-533544, dated Jun. 19, 2012, 3 pages total.

Summons to Attend Oral Proceedings of EP Patent Application No. 07844424.7, dated Jul. 5, 2012, 7 pages total.

European Search Report and Search Opinion of EP Patent Application No. 11191822.3, dated Jun. 13, 2012, 13 pages total.

Office Action issued in European Application No. 07844421.3, dated Aug. 23, 2012, 5 pages total.

Notice of the Reason for Refusal issued in Japanese Patent Application No. 2009-533546, dated Jun. 19, 2012, 6 pages total.

Extended European Search Report and Search Opinion of EP Patent Application No. 12154069.4, dated Sep. 17, 2012, 13 pages total.

Notice of the Reason for Refusal issued in Japanese Patent Application No. 2006-526351, dated Sep. 18, 2012, 20 pages total.

Office Action issued in Chinese Patent Application No. 201110031923. X, dated Sep. 6, 2012, 11 pages total.

Office Action in Australian Patent Application No. 2010248955, dated Sep. 13, 2012, 4 pages total.

Brown et al., "Radiofrequency capacitive heaters: the effect of coupling medium resistivity on power absorption along a mouse leg," Physics in Medicine and Biology, p. 1-12, vol. 38, 1993.

Cardiovascular Technologies, Inc., "Heated Balloon Device Technology," [Presentation], 11 pages total. Retrieved from: <<http://www.cvtechnic.com/pr/presoCVT_Heated_Balloon_Tech.pdf>> 2007-2008.

Carrington, "Future of CVI: It's All About the Plaque," Diagnostic Imaging Special Edition Forum [online] [retrieved on Sep. 3, 2003] Retrieved from the Internet:, http://dimag.com/specialedition/cardiacimg.shtml> 5 pages total.

Cimino, "Preventing Plaque Attack," [online] [retrieved on Sep. 3, 2003] retrieved from the Internet: <http://Masshightech.com/displayarticledetail.ap?art_id=52283&cat_id=10>, 3 pages total.

Dahm et al., "Relation of Degree of Laser Debulking of In-Stent Restenosis as a Predictor of Restenosis Rate," The American Journal of Cardiology, p. 68-70, vol. 90, 2002.

De Korte et al., "Characterization of Plaque Components With Intravascular Ultrasound Elastography in Human Femoral and Coronary Arteries in Vitro," Circulation, p. 617-623, 2000.

Durney et al., "Radiofrequency Radiation Dosimetry Handbook," (with table of contents) 4th edition, 7 pages, Armstrong Laboratory (AFMC) Occupational and Environmental Health Directorate Radiofrequency Radiation Division, USAF School of Aerospace Medicine, Aerospace Medical Division (AFSC), Brooks Air force Base, http://www.brooks.af.mil/AFRL/HED/hedr/reports/handbook/home.htm, Oct. 1986.

Fournier-Desseux et al., "Assessment of 1-lead and 2-lead electrode patterns in electrical impedance endotomography," Physiological Measurement, p. 337-349. Vol. 26, Institute of Physics Publishing, 2005.

Fujimori et al., "Significant Prevention of In-Stent Restenosis by Evans Blue in Patients with Acute Myocardial Infarction," Abstract #2925. AHA, 2002.

Fujita et al., "Sarpogrelate, An Antagonist of 5-HT(2A) Receptor, Treatment Reduces Restenosis After Coronary Stenting," Abstract #2927, AHA, 1 page total, 2002.

Gabriel et al; Compliation of the Dielectric Properties of Body Tissues at RF and Microwave Frequencies (with table of contents), Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html, 17 pages, Jun. 1996.

Gabriel et al; "Compliation of the Dielectric Properties of Body Tissues at RF and Microwave Frequencies," Appendi04-10-2009 A, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://broks.af.mil/AFRL/HED/hedr/reports/dielectric/Appendi04-10-2009.A/Appendi04-10-2009 A.html. 21 pages, Jun. 1996.

Gabriel et al; "Compliation of the Dielectric Properties of Body Tissues at RF and Microwave Frequencies," Appendi04-10-2009 C, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.C/Appendi04-Oct. 2009 C.html. 6 pages, Jun. 1996.

Gregory et al., "Liquid Core Light Guide for Laser Angioplasty," The Journal of Quantum Electronics, p. 2289-2296, vol. 26, No. 12. Dec. 1990.

Intraluminal, Product description [online] Retrieved from the Internet: http://www.intraluminal.com/products/nde04-10-2009.html> 1 page total, [retrieved on Sep. 3, 2003].

(56) References Cited

OTHER PUBLICATIONS

Kaplan et al., "Healing after Arterial Dilatation with Radiofrequency Thermal and Nonthermal Balloon Angioplasty Systems," Journal of Investigative Surgery, p. 33-52, vol. 6. Jan., Feb. 1993.
Kolata, "New Studies Question Value of Opening Arteries," The New York Times [online] Retrieved from the Internet http://nytimes.com/2004/03/21/health/21HEAR.html?ei=5070&en=641bc03214e&e04-10-29-11067>5 pages total, [Retrieved on Jan. 25, 2005].
Konings et al., "Development of an Intravascular Impedance Catheter for Detection of Fatty Lesions in Arteries," IEEE Transactions on Medical Imaging, vol. 51, No. 4, Apr. 2004.
Kurtz et al., "Lamellar Refractive Surgery with Scanned Intrastromal Picosecond and Femtosecond Laser Pulses in Animal Eyes," Journal of Refractive Surgery, p. 541-548. Sep./Oct. 1998.
Lightlab Imaging Technology, "Advantages of OCT," [online] Retrieved from the Internet: <http:www.lightlabimaging.com/advantage.html> 2 pages total, [Retrieved on Sep. 3, 2003].
Lightlab Imaging Technology, "Image Gallery," [online] Retrieved from the Internet: <http:lightlabimaging.com/gallery/cvpstill.html> 4 pages total, [Retrieved on Sep. 3, 2003].
LightLab Imaging Technology, "Lightlab Sees Bright Prospects for Cardiac Application of OCT Technology," The Graysheet Medical Devices & Instrumentation, vol. 27, No. 35. Retrieved from the Internet: <http://www.lightlabimaging.com/press/graysheet.html>1 page total. Aug. 27, 2001, Retrieved on Sep. 3, 2003.
LightLab Imaging Technology, "What is OCT?" [online] Retrieved from the Internet: <http:lightlabimaging.com/oct.html.> 2 pages total. Retrieved on Sep. 3, 2003.
LightLab Imaging Technology, "Why use OCT?", [online] Retrieved from the Internet: <http:lightlabimaging.com/whyoct/html.> 2 pages total, [Retrieved on Sep. 3, 2003].
LightLab Imaging Technology, "LightLab imaging Starts US Cardiology Clinical Investigations," LightLab Company Press Release, [online] Retrieved from the Internet:http://www.lightlabimaging.com/press/cardtrails.html>2 pages total, Retrieved on Sep. 3, 2003.
Lima et al., "Efficacy and Safety of Oral Sirolimus to Treat and Prevent In-Stent Restenosis: a Pilot Study Results," Abstract #2929, 1 page total, AHA 2002.
Lima et al., "Systemic Immunosuppression Inhibits In-Stent Coronary Intimal Proliferation in Renal Transplant Patients," Abstract #2928, AHA 1 page total, 2002.
MIT Techtalk, "Laser Catheter to Aid Coronary Surgery," Retrieved from the Internet: <http://web.mit.edu/newsoffice/tt/1991/jan9/24037.html> 4 pages, Jan. 9, 1991 [online] [Retrieved on Feb. 7, 2005.].
Morice et al., "A Randomized Comparison of a Sirolimus-Eluting Stent With a Standard Stent for Coronary Revascularization," The New England Journal of Medicine, p. 1773-1780, vol. 346, No. 23, Jun. 6, 2012.
Muller-Leisse et al., "Effectiveness and Safety of Ultrasonic Atherosclerotic Plaque Ablation: in Vitro Investigation," CardioVascular and Interventional Radiology, p. 303-307, vol. 16, 1993.
Nair et al., "Regularized Autoregressive Analysis of Intravascular Ultrasound Backscatter: Improvement in Spatial Accuracy of Tissue Maps," IEEE Transactions on Ultrasonics, Ferroelectrics and Frequency Control, vol. 51, No. 4. Apr. 2004.
Popma et al., "Chapter 38—Percutaneous Coronary and Valvular Intervention," Heart Disease: a Textbook of Cardiovascular Medicine 6th edition WB Saunders Company p. 1364-1405, 2001.
Romer et al., "Histopathology of Human Coronary Atherosclerosis by Quantifying Its Chemical Composition With Raman Spectroscopy," Circulation, p. 878-885, vol. 97, 1998.
Scheller et al., "Potential Solutions to the Current Problem: Coated Balloon," EuroIntervention, p. C63-C66, vol. 4 (Supplement C), Aug. 2008.
Scheller et al., "Intracoronary Paclitaxel Added to Contrast Media Inhibits In-Stent Restenosis of Porcine Coronary Arteries," Abstract #2227, 2 pages total, AHA 2002.
Shaffer, "Scientific Basis of Laser Energy," Clinics in Sports Medicine, p. 585-598, vol. 21(4) 2002.

Shmatukha et al., "MRI Temperature Mapping during Thermal Balloon Angioplasty," Physics in Medicine and Biology, vol. 51, p. N163-N171, 2006.
Slager et al., "Vaporization of Atherosclerotic Plaques by Spark Erosion," vol. 5, pp. 1382-1386, J Am Coll Cardiol, 1985.
Stiles et al., "Simulated Characterization of Atherosclerotic Lesions in the Coronary Arteries by Measurement of Bioimpedance," IEEE Transactions on Biomedical Engineering, 5(4) p. 916-921, Jul. 2003.
Suselbeck et al., "Intravascular Electric Impedance Spectroscopy of Atherosclerotic Lesions using a New Impedance Catheter System," Basic Res Cardiol, vol. 100, p. 446-452, 2005.
Suselbeck et al., "In Vivo Intravascular Electric Impedance Spectroscopy using a New Catheter with Integrated Microelectrodes," Basic Res Cardiol, vol. 100,p. 28-34, 2005.
Tepe et al., "Local Delivery of Paclitaxel to Inhibit Restenosis during Angioplasty of the Leg," The New England Journal of Medicine, 358(7) p. 689-699, Retrieved from the Internet <<http://content.nejm.org/cgi/reprint/357/7/689.pdf>> Feb. 14, 2008.
Van Den Berg, "Light Echoes Image the Human Body," OLE, p. 35-37, Oct. 2001.
Volcano Therapeutics, Product—Functional Measurement [online] Retrieved from the Internet :<http://www.volcanotherapeutics.com/pages/products/functional_measurement-us.html>2 pages total, [Retrieved on Sep. 3, 2003].
Examiner's Report of Canadian Patent Application No. 2,539,026, dated Feb. 6, 2012, 4 total pages.
Office Action issued in Chinese Patent Application No. 200480030163.9 dated Jan. 16, 2009, 8 pages total.
Office Action issued in Chinese Patent Application No. 200480030163.9 dated Mar. 28, 2008, 7 pages total.
Office Action issued in Chinese Patent Application No. 200480030163.9 dated Aug. 31, 2007, 8 pages total.
Office Action issued in Chinese Patent Application No. 200480030163.9 dated Jul. 31, 2009, 5 pages total.
Supplementary Partial European Search Report of Application No. 04816863.7, dated May 8, 2009, 7 pages total.
Office Action issued in European Application No. 048168636.7, dated Jun. 4, 2010, 5 pages total.
Office Action issued in Chinese Patent Application No. 200480030163.9 dated Dec. 5, 2011, 4 total pages.
Office Action issued in Chinese Patent Application No. 200480030163.9 dated Jan. 22, 2010, 6 total pages.
Formal Inquiry issued in Japanese Patent Application No. 2006-526351, dated Jan. 17, 2012, 5 pages total.
Notice of Reason for Refusal issued in Japanese Patent Application No. 2006-526351, dated Apr. 27, 2010, 6 pages total.
Final Decision of Rejection in Japanese Patent Application No. 2006-526351, dated Jan. 18, 2011, 4 pages total.
European Search Report and Search Opinion of EP Patent Application No. 12151957.3, dated Apr. 16, 2012, 8 pages total.
Office Action issued in Chinese Patent Application No. 200680016424.0, dated Apr. 13, 2010, 10 pages total.
European Search Report and Search Opinion of EP Patent Application No. 06748830.4, dated Nov. 16, 2009, 12 pages total.
Partial European Search Report of EP Patent Application No. 11191822.3, dated Mar. 19, 2012, 7 pages total.
Office Action issued in Chinese Patent Application No. 20111031923.X, dated Nov. 17, 2011, 16 pages total.
Examiner's First Report of Australian Patent Application No. 2007310988, dated May 23, 2012, 4 pages total.
European Search Report and Search Opinion of EP Patent Application No. 07844421.3, dated Jan. 4, 2010, 15 pages total.
European Search Report and Search Opinion of EP Patent Application No. 12155447.1, dated May 10, 2012, 6 pages total.
International Search Report and Written Opinion of PCT Application PCT/US2009/064027, dated Jan. 19, 2010, 9 pages total.
European Search Report and Search Opinion of EP Patent Application No. 07844417.1, dated Nov. 5, 2009.
European Search Report and Search Report of EP Patent Application No. 12154120.5, dated May 8, 2012, 8 pages total.
European Search Report and Search Opinion of EP Patent Application No. 07844424.7, dated Nov. 11, 2009, 11 pages total.

(56) References Cited

OTHER PUBLICATIONS

Partial European Search Report of EP Patent Application No. 12154069.4, dated May 10, 2012, 5 pages total.
International Search Report and Written Opinion of PCT Application No. PCT/US2009/064465, dated Jan. 13, 2010, 13 pages total.
International Search Report of PCT Application No. PCT/US09/57728, dated Nov. 30, 2009, 10 pages total.
International Search Report and Written Opinion of PCT/US2010/034789, dated Jul. 9, 2010, 13 pages total.
International Search Report and Written Opinion of PCT/US2011/00661, dated Nov. 18, 2011, 14 pages total.
Fry, "Thermal and Disruptive Angioplasty: a Physician's Guide," Strategic Business Development Inc. 8 pages, 1990.
Zhang et al; "Non-Contact Radio-Frequency for Obtaining Deeper Lesions," IEEE Transaction on Biomedical Engineering, vol. 50, No. 2, 6 pages, Feb. 2003.
Lazebnik et al; "Tissue Strain Analytics Virtual Touch Tissue Imaging and Qualification," Siemens Whitepaper, 7 pages, Oct. 2008.
Han et al; "Third-Generation Cryosurgery for Primary and Recurrent Prostate Cancer," BJU International, vol. 93, pp. 14-18, 2004.
Zhou et al; Mechanism Research of Cryoanalgesia, Forefont Publishing Group, 1995.
Florete, "Cyoblative Procedure for Back Pain," Jacksonville Medicine, 10 pages, Oct. 1998.
Stevenson, "Irrigated RF Ablation:Power Titration and Fluid Management for Optimal Safety Efficacy," 4 pages, 2005.
Giliatt et al; "The Cause of Nerve Damage in Acute Compression," Trans Am Neurol Assoc 99; 71-4, 1974.
Omura et al; "A Mild Acute Compression Induces Neurapraxia in Rat Sciatic Nerve," The International Journal of Neuroscience, vol. 144(12) pp. 1561-1572, Dec. 2004.
Baun, Interaction with Soft Tissue, Principles of general & Vascular Sonography, Chapter 2, pp. 23-24, Before Mar. 2012.
Blue Cross Blue Shield Medical Policy, "Surgery Section—MRI Guided Focused Ultrasound (MRgFUS) for the Treatment of Uterine Fibroids and Other Tumors," 5 pages, 2005.
Gentry et al; "Combines 3D Intracadiac Echo and Ultrasound Ablation," Medical Imaging 2003: Ultrasonic and Signal Processing, vol. 5035, pp. 166-173, 2003.
Lafon et al; "Optimizing the Shape of Ultrasound Transducers for Interstitial Thermal Ablations," MEd Phys. 29(3): 290-7, (abstract only) Mar. 2002.
G. Ter Haar, "Ultrasound Focal Beam Surgery," Ultrasound in Med. & Biol. vol. 21, No. 9, pp. 1089-1100, 1995.
Seip et al; "Transurethral High Intensity Focused Ultrasound Catheter Based Prototypes and Experimental Results," IEEE Ultrasonics Symposioum Proceeding, 4 pages, 2000.
Toytman et al; "Tissue Dissection with Ultrafast Laser Using Extended and Multiple Foci," SPIE Proceeding, Optical Interactions with Tissues and Cells XXI, vol. 7562, 10 pages, 2010.
Zhoue et al; "Non-Thermal Ablation of Rabbit Liver VX2 Tumore by Pulsed High Intensity Focused Ultrasound Contrast Agent: Pathological Characteristics," World Journal of Gastroenterology, vol. 14(43), pp. 6743-6747, Nov. 21, 2008.
Chen et al; "Percutaneous Pulmonary Artery Denervation Completely Abolishes Pulmonary Hypertension in Vivo," EuroIntervention, pp. 1-8, 2013.
Fram et al; "Feasibility of Radiofrequency Powered, Thermal, Balloon Ablation of Atrioventricular Bypass Tracts Via the Coronary Sinus: in Vivo Canine Studies," PACE, vol. 18, pp. 1518-1530, Aug. 1995.
Fram et al; "Low Pressure Radiofrequency Balloon Angioplasty: Evaluation in Porcine Peripheral Arteries," JACC vol. 21, No. 6, pp. 1512-1521, American College of Cardiology, 1993.
Lee et al; "Thermal Compression and Molding of Athersclerotic Vascular Tissue with Use of Radiofrequency Energy: Implications for Radiofrequency Balloon Angioplasty," JACC vol. 13, No. 5, p. 1167-1175, American College of Cardiology, 1989.
Gabriel, "Appendix A: Experimental Data," p. 1-21, 1999.
Gabriel, "Appendix C: Modeling the Frequency Dependence of the Dielectric Properties to a 4 Dispersions Spectrum," p. 1-6, No year listed.

\* cited by examiner

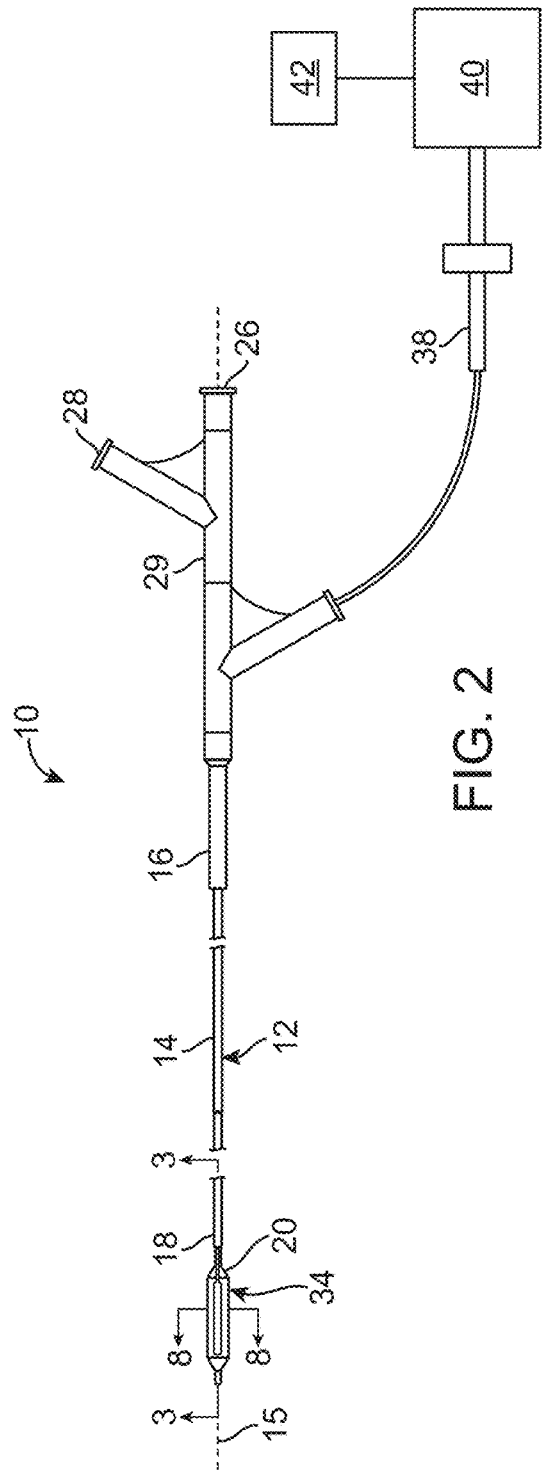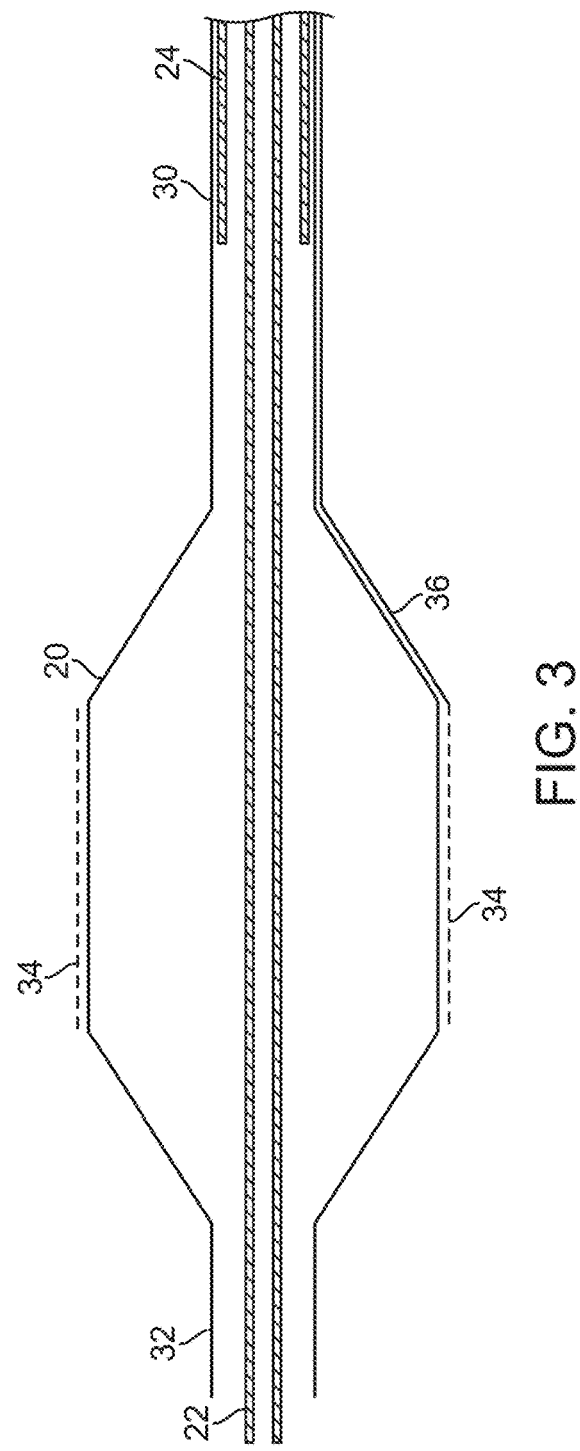

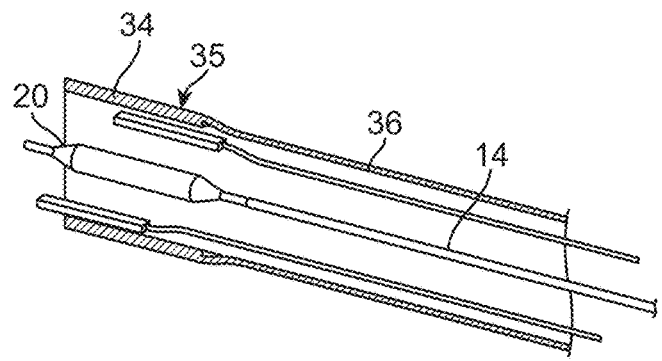
FIG. 5A
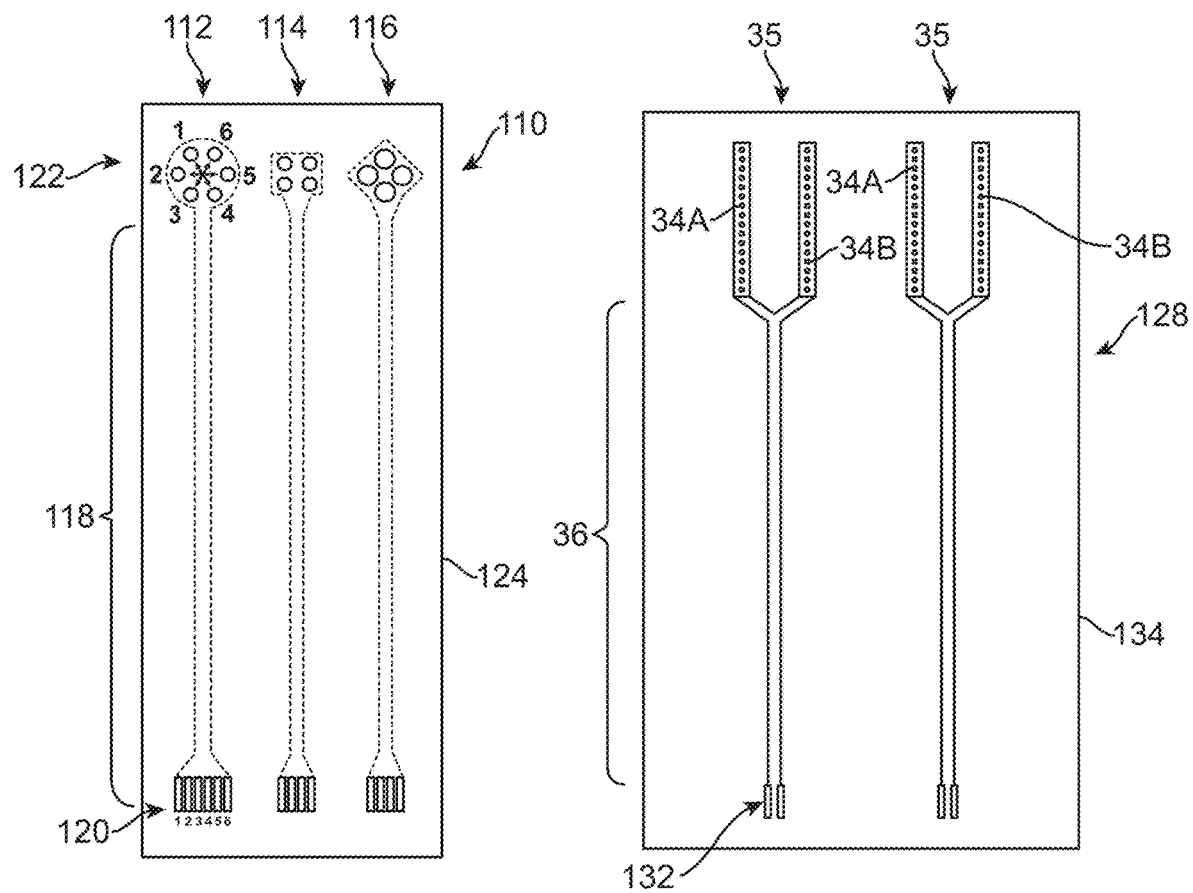
FIG. 5B
FIG. 5C

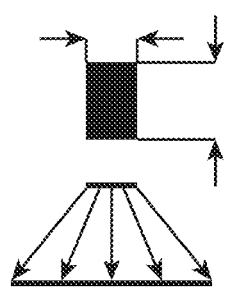
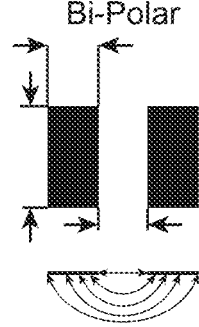
FIG. 12A    FIG. 12B
FIG. 13    FIG. 14
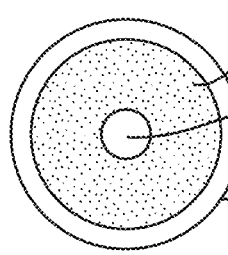
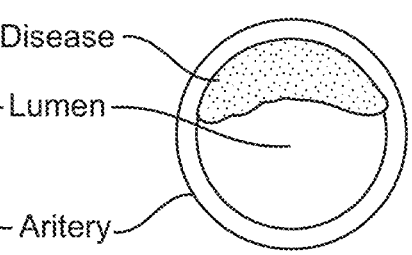
FIG. 15A    FIG. 15B

SYSTEM FOR INDUCING DESIRABLE TEMPERATURE EFFECTS ON BODY TISSUE

CROSS-REFERENCES TO RELATED APPLICATIONS

This application is a continuation of U.S. patent application Ser. No. 13/385,555, filed Feb. 24, 2012, which is a continuation of and claims the benefit of U.S. patent application Ser. No. 11/975,383 filed Oct. 18, 2007, which claims the benefit under 35 USC 119(e) of U.S. Provisional Application No. 60/852,787, filed on Oct. 18, 2006, and entitled "Tuned RF Energy And Electrical Tissue Characterization For Selective Treatment Of Target Tissues"; U.S. Provisional Application No. 60/921,973, filed on Apr. 4, 2007, and entitled "Tuned RF Energy And Electrical Tissue Characterization For Selective Treatment Of Target Tissues", and U.S. Provisional Application No. 60/976,733, filed on Oct. 1, 2007, entitled "System for Inducing Desirable Temperature Effects On Body Tissue", the full disclosures of which are incorporated herein by reference.

This application is related to U.S. patent application Ser. No. 11/392,231, filed on Mar. 28, 2006, entitled "Tuned RF Energy for Selective Treatment of Atheroma and Other Target Tissues and/or Structures"; U.S. patent application Ser. No. 10/938,138, filed on Sep. 10, 2004, and entitled "Selectable Eccentric Remodeling and/or Ablation of Atherosclerotic Material"; U.S. Patent Application No. 60/852,787, filed on Oct. 18, 2006, entitled "Tuned RF Energy And Electrical Tissue Characterization For Selective Treatment Of Target Tissues"; U.S. Provisional Application No. 60/921,973, filed on Apr. 4, 2007, entitled "Tuned RF Energy And Electrical Tissue Characterization For Selective Treatment Of Target Tissues", and U.S. Provisional Application No. 60/976,752, filed on Oct. 1, 2007, entitled "Inducing Desirable Temperature Effects on Body Tissue" the full disclosures of which are incorporated herein by reference.

BACKGROUND OF THE INVENTION

Field of the Invention

The present invention is generally related to medical devices, systems, and methods. In exemplary embodiments, the invention provides catheter-based treatment for luminal diseases, particularly for atherosclerotic plaque, vulnerable or "hot" plaque, and the like. The structures of the invention allow remodeling body tissue using heat.

Physicians use catheters to gain access to and repair interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) which may also improve the procedural angioplasty success rates.

While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

In light of the above, it would be advantageous to provide new devices, systems, and methods for remodeling of the lumens of the body, and particularly of the blood vessels. It would further be desirable to avoid significant cost or complexity while providing structures which could remodel body lumens without having to resort to the trauma of extreme dilation, and to allow the opening of blood vessels and other body lumens which are not suitable for stenting.

BRIEF SUMMARY OF THE INVENTION

The present invention generally provides improved devices, systems, and methods for treating diseased and other target tissues, optionally for treatment of diseases of body lumens. Embodiments of the invention allow heating the body lumens. By radially expanding a balloon with electrodes, plaque, fibrous vulnerable or "hot" plaques, along with healthy tissues are heated by the energized electrodes using RF energy, microwave energy, ultrasound energy, and/or the like.

In one embodiment, a system is disclosed for inducing desirable temperature effects on body tissue disposed about a lumen. The system includes a catheter body having a proximal end and a distal end, with a radially expandable member on the distal end. The expandable member has a low profile insertion configuration and a larger profile configuration. A plurality of electrodes are disposed about the expandable member so as to define a plurality of tissue volumes ("remodeling zones") when the expandable member is in the large profile configuration within the lumen. The electrodes are radially coupled with the tissue, and energy intended to remodel the tissue ("tissue remodeling energy") is transmitted between the electrodes and the tissue, the electrodes configured to inhibit vaporization along the lumen while the remodeling energy inhibits both acute and long-term occlusion of the lumen.

In another embodiment, a method for using a catheter system is disclosed for inducing desirable temperature effects on desired body tissue disposed about a lumen of a patient. The method includes positioning a radially expandable member supported by a distal end of a catheter body within the lumen adjacent the desired tissue to be heated, the expandable member having a low profile insertion configuration and a larger profile configuration. Expanding the expandable member to the larger profile configuration within the lumen so as to engage a plurality of electrodes against the desired tissue, the plurality of electrodes defining a plurality of remodeling zones in the tissue. Energizing the plurality of electrodes with a controller having a power source electrically coupled to the plurality of electrodes and heating the remodeling zones in the tissue with the energized electrodes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 schematically illustrates a balloon catheter system according to the present invention.

FIG. 3 schematically illustrates one embodiment of an inflatable balloon for use in the catheter system of FIG. 2.

FIG. 5A schematically illustrates one embodiment of electrodes in a circumferential array mounting to a balloon.

FIGS. 5B and 5C schematically illustrates electrodes in flexible circuit/circuitry.

FIG. 12A schematically illustrates a mono-polar configuration.

FIG. 12B schematically illustrates a bipolar configuration.

FIG. 13 schematically illustrates electrodes arranged on a balloon in a radial topology.

FIG. 14 schematically illustrates electrodes arranged on a balloon in a longitudinal topology.

FIG. 15A schematically illustrates diseased tissue that is concentric about the entire circumference of an artery.

FIG. 15B schematically illustrates diseased tissue that is eccentric about a portion of an artery along with healthy tissue.

DETAILED DESCRIPTION OF THE INVENTION

Figure 1A:
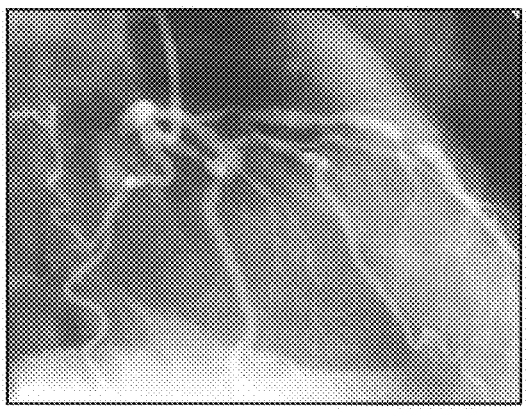
FIG. 1A illustrates diffuse atherosclerotic disease in which a substantial length of multiple blood vessels has limited effective diameters.

The present invention provides devices, systems, and methods to treat luminal tissue. The invention will be particularly useful for remodeling materials along a partially occluded artery in order to open the artery lumen and increase blood flow. The devices, systems, and methods disclosed herein may be used in any artery, for example, the femoral, popliteal, coronary and/or carotid arteries.

While the disclosure focuses on the use of the technology in the vasculature, the technology would also be useful for any luminal obstruction. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Some embodiments of the vascular treatment devices, systems, and methods described herein may be used to treat atherosclerotic disease by gentle heating in combination with gentle or standard dilation. For example, an angioplasty balloon catheter structure having electrodes disposed thereon might apply electrical potentials to the vessel wall before, during, and/or after dilation, optionally in combination with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flexible circuit electrodes on the balloon, electrodes deposited directly on the balloon structure, or the like)

described herein may employ from 10-16 atmospheres or may be effected with pressures of 6 atmospheres or less, and possibly as low as 1 to 2 atmospheres. Such moderate dilations pressures may (or may not) be combined with one or more aspects of the tissue characterization, tuned energy, eccentric treatments, and other treatment aspects described herein for treatment of diseases of the peripheral vasculature.

In many embodiments, gentle heating energy added before, during, and or after dilation of a blood vessel may increase dilation effectiveness while lowering complications. In some embodiments, such controlled heating with balloon may exhibit a reduction in recoil, providing at least some of the benefits of a stent-like expansion without the disadvantages of an implant. Benefits of the heating may be enhanced (and/or complications inhibited) by limiting heating of the adventitial layer below a deleterious response threshold. In many cases, such heating of the intima and/or media may be provided using heating times of less than about 10 seconds, often being less than 3 (or even 2) seconds. In other cases, very low power may be used for longer durations. Efficient coupling of the energy to the target tissue by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

Remodeling may involve the application of energy, typically in the form of RF, microwave and/or ultrasound energy to electrodes, and the like. This energy will be controlled so as to limit a temperature of target and/or collateral tissues, for example, limiting the heating of a fibrous cap of a vulnerable plaque or the intimal layer of an artery structure. In some embodiments, the surface temperature range is from about 50° C. to about 90° C. For gentle heating, the surface temperature may range from about 50° C. to about 65° C., while for more aggressive heating, the surface temperature may range from about 65° C. to about 90° C. Limiting heating of a lipid-rich pool of a vulnerable plaque sufficiently to induce melting of the lipid pool while inhibiting heating of other tissues (such as an intimal layer or fibrous cap) to less than a surface temperature in a range from about 50° C. to about 65° C., such that the bulk tissue temperature remains mostly below 50° C.-55° C. may inhibit an immune response that might otherwise lead to restenosis, or the like. Relatively mild surface temperatures between 50° C. and 65° C. may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

While the methods and devices described herein are not selective in tissue treatment of the blood vessel, the devices can be used for treatment of both concentric and eccentric atherosclerosis. This non selective treatment is a particular advantage because atherosclerosis may be eccentric relative to an axis of the blood vessel over 50% of the time, possibly in as much as (or even more than) 75% of cases.

Hence, remodeling of atherosclerotic materials may comprise shrinkage, melting, and the like of atherosclerotic and other plaques. Atherosclerotic material within the layers of an artery may be denatured, melted and/or the treatment may involve a shrinking of atherosclerotic materials within the artery layers so as to improve blood flow. The invention may also provide particular advantages for treatment of vulnerable plaques or blood vessels in which vulnerable plaque is a concern, which may comprise eccentric lesions. The invention will also find applications for mild heating of the cap structure (to induce thickening of the cap and make the plaque less vulnerable to rupture) and/or heating of the lipid-rich pool of the vulnerable plaque (so as to remodel, denature, melt, shrink, and/or redistribute the lipid-rich pool).

While the present invention may be used in combination with stenting, the present invention is particularly well suited for increasing the open diameter of blood vessels in which stenting is not a viable option. Potential applications include treatment of diffuse disease, in which atherosclerosis is spread along a significant length of an artery rather than being localized in one area. The invention may also find advantageous use for treatment of tortuous, sharply-curved vessels, as no stent need be advanced into or expanded within the sharp bends of many blood vessel. Still further advantageous applications include treatment along bifurcations (where side branch blockage may be an issue) and in the peripheral extremities such as the legs, feet, and arms (where crushing and/or stent fracture failure may be problematic).

In some instances, it may be desirable to obtain baseline measurements of the tissues to be treated (which may be characterized via intravascular ultrasound, optical coherence tomography, or the like) may be taken to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues. Any of the techniques disclosed in U.S. Patent Application No. 60/852,787, entitled "Tuned RF Energy And Electrical Tissue Characterization For Selective Treatment Of Target Tissues"; and U.S. Provisional Application No. 60/921,973, filed on Apr. 4, 2007, entitled "Tuned RF Energy And Electrical Tissue Characterization For Selective Treatment Of Target Tissues", the full disclosures of which are incorporated herein by reference, may be combined with the present invention.

Figure 1B:
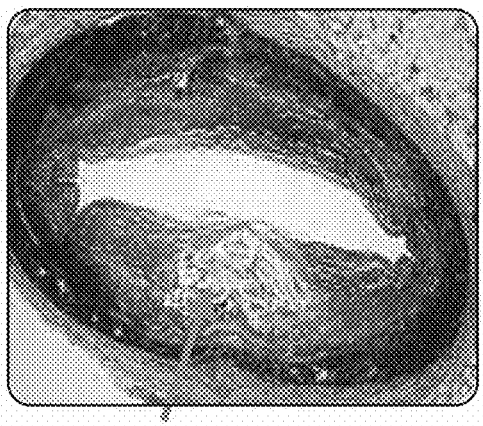
FIG. 1B illustrates vulnerable plaque within a blood vessel.
Figure 1C:
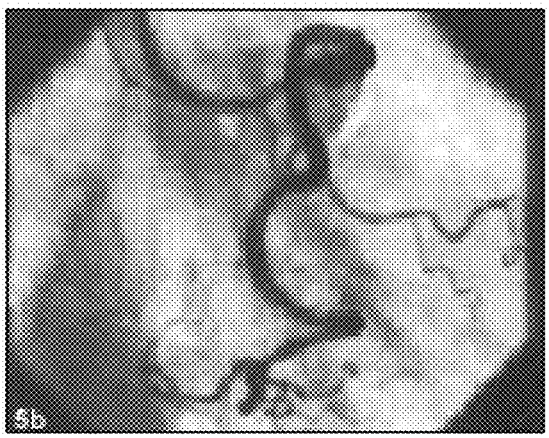
FIG. 1C illustrates the sharp bends or tortuosity of some blood vessels.
Figure 1D:
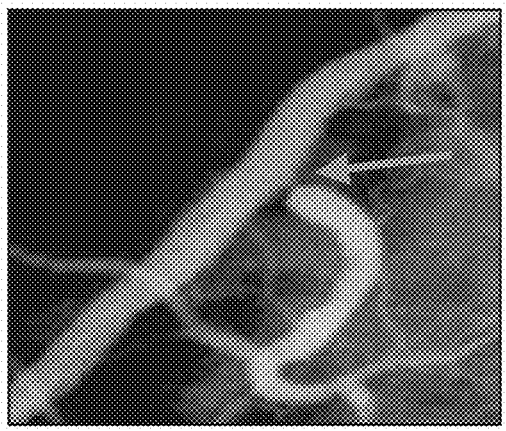
FIG. 1D illustrates atherosclerotic disease at a bifurcation.
Figure 1E:
FIG. 1E illustrates a lesion associated with atherosclerotic disease of the extremities.

Diffuse disease and vulnerable plaque are illustrated in FIGS. 1A and 1B, respectively. FIG. 1C illustrates vascular tortuosity. FIG. 1D illustrates atherosclerotic material at a bifurcation, while FIG. 1E illustrates a lesion which can result from atherosclerotic disease of the extremities.

Figure 1F:
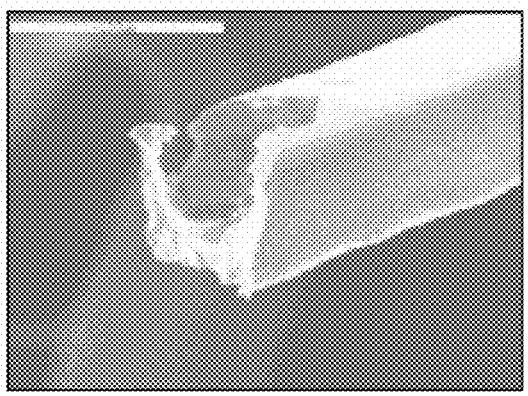
FIG. 1F is an illustration of a stent fracture or corrosion.

FIG. 1F illustrates a stent structural member fracture which may result from corrosion and/or fatigue. Stents may, for example, be designed for a ten-year implant life. As the population of stent recipients lives longer, it becomes increasingly likely that at least some of these stents will remain implanted for times longer than their designed life. As with any metal in a corrosive body environment, material degradation may occur. As the metal weakens from corrosion, the stent may fracture. As metal stents corrode, they may also generate foreign body reaction and byproducts which may irritate adjoining body tissue. Such scar tissue may, for example, result in eventual reclosure or restenosis of the artery.

Figure 1G:
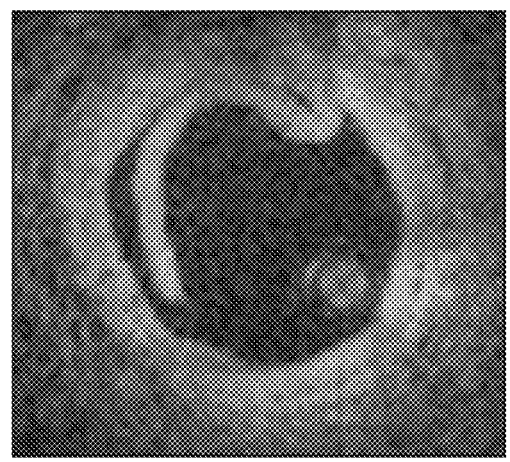
FIG. 1G illustrates a dissection within a blood vessel.
Figure 1H:
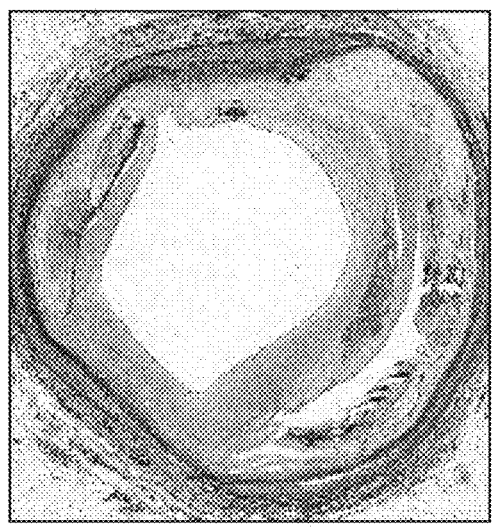
FIG. 1H illustrates an artery wall around a healthy artery.
Figure 1I:
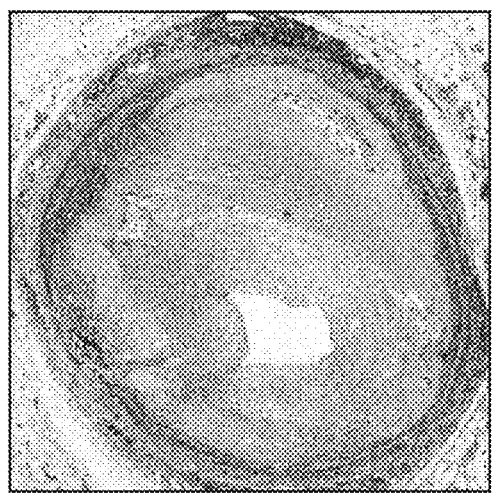
FIG. 1I illustrates a restenosed artery.

Arterial dissection and restenosis may be understood with reference to FIGS. 1G through 1I. The artery comprises three layers, an endothelial layer, a medial layer, and an adventitial layer. During traditional angioplasty, the inside layer may delaminate or detach partially from the wall so as to form a dissection as illustrated in FIG. 1G. Such dissections divert and may obstruct blood flow. FIG. 1H illustrates an artery wall around a healthy artery and FIG. 1I illustrates a restenosed artery. As can be understood by comparing FIGS. 1H and 1I, traditional angioplasty is a relatively aggressive procedure which may injure the tissue of the blood vessel. In response to this injury, in response to the presence of a stent, and/or in the continuing progression of the original atherosclerotic disease, the opened artery may restenose or subsequently decrease in diameter as illustrated in FIG. 1I. While drug eluting stents have been shown to reduce restenosis, the efficacy of these new structures several years after implantation has not be fully studied, and such drug eluting stents are not applicable in many blood vessels.

In general, the present invention provides a catheter system which is relatively quick and easy to use by the physician. The catheter system of the present invention uses mild heat to provide tissue surface temperatures in a range between about 50° C. and 65° C. to gently remodel the tissue, that may allow arteries to be opened.

FIG. 2 shows one embodiment of a catheter system 10 for inducing desirable temperature effects on artery tissue. The catheter system 10 includes a balloon catheter 12 having a catheter body 14 with a proximal end 16 and a distal end 18. Catheter body 14 is flexible and defines a catheter axis 15, and may include one or more lumens, such as a guidewire lumen 22 and an inflation lumen 24 (see FIG. 3). Still further lumens may be provided if desired for other treatments or applications, such as perfusion, fluid delivery, imaging, or the like. Catheter 12 includes an inflatable balloon 20 adjacent distal end 18 and a housing 29 adjacent proximal end 16. Housing 29 includes a first connector 26 in communication with guidewire lumen 22 and a second connector 28 in fluid communication with inflation lumen 24. Inflation lumen 24 extends between balloon 20 and second connector 28. Both first and second connectors 26, 28 may optionally comprise a standard connector, such as a Luer-Loc™ connector. A distal tip may include an integral tip valve to allow passage of guidewires, and the like.

Housing 29 also accommodates an electrical connector 38. Connector 38 includes a plurality of electrical connections, each electrically coupled to electrodes 34 via conductors 36. This allows electrodes 34 to be easily energized, the electrodes often being energized by a controller 40 and power source 42, such as bipolar or monopolar RF energy, microwave energy, ultrasound energy, or other suitable energy sources. In one embodiment, electrical connector 38 is coupled to an RF generator via a controller 40, with controller 40 allowing energy to be selectively directed to electrodes 38. When monopolar RF energy is employed, patient ground may (for example) be provided by an external electrode or an electrode on catheter body 14.

In some embodiments, controller 40 may include a processor or be coupled to a processor to control or record treatment. The processor will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor via one or more bus, and appropriate standard or proprietary communications cards, connectors, cables, and the like will often be included in the processor. Processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modem computer systems may also be included, and processors having a plurality of processing units (or even separate computers) may be employed in a wide range of centralized or distributed data processing architectures.

Balloon 20 is illustrated in more detail in FIG. 3. Balloon 20 generally includes a proximal portion 30 coupled to inflation lumen 24 and a distal portion 32 coupled to guidewire lumen 22. Balloon 20 expands radially when inflated with a fluid or a gas. In some embodiments, the fluid or gas may be non-conductive and/cooled. In some embodiments, balloon 20 may be a low pressure balloon pressurized to contact the artery tissue. In other embodiments, balloon 20 is an angioplasty balloon capable of higher pressure to both heat the artery tissue and expand the artery lumen. Balloon 20 may comprise a compliant or non-compliant balloon having helical folds to facilitate reconfiguring the balloon from a radially expanded, inflated configuration to a low profile configuration, particularly for removal after use.

Electrodes 34 are mounted on a surface of balloon 20, with associated conductors 36 extending proximally from the electrodes. Electrodes 34 may be arranged in many different patterns or arrays on balloon 20. The system may be used for monopolar or bipolar application of energy. For delivery of monopolar energy, a ground electrode is used, either on the catheter shaft, or on the patients skin, such as a ground electrode pad. For delivery of bipolar energy, adjacent electrodes are axially offset to allow bipolar energy to be directed between adjacent circumferential (axially offset) electrodes. In other embodiments, electrodes may be arranged in bands around the balloon to allow bipolar energy to be directed between adjacent distal and proximal electrodes.

Figure 4A:
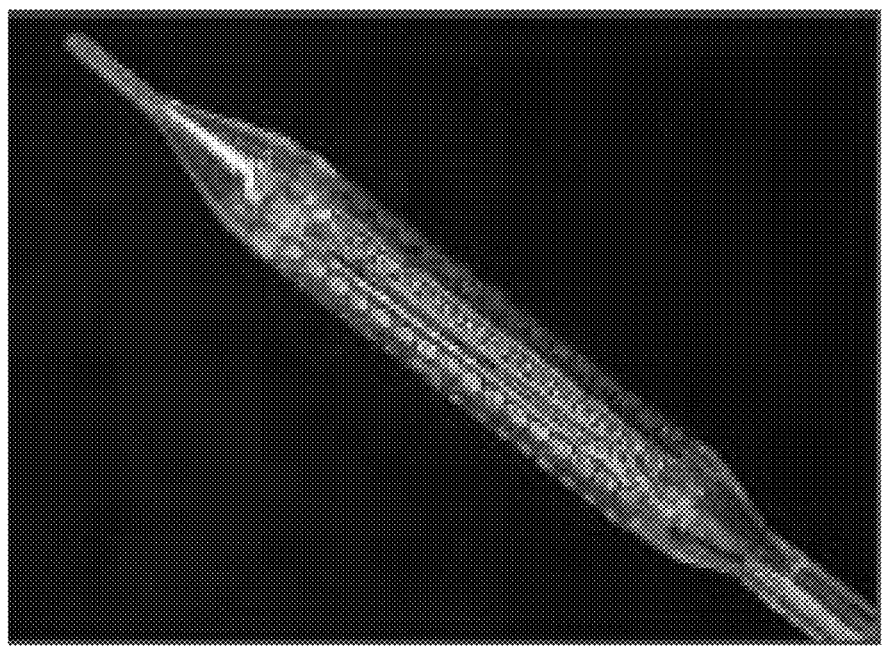
FIGS. 4A and 4B show an exemplary balloon catheter supporting electrodes and an exemplary RF generator structure, respectively, for use in the systems and methods described herein.
Figure 4B:
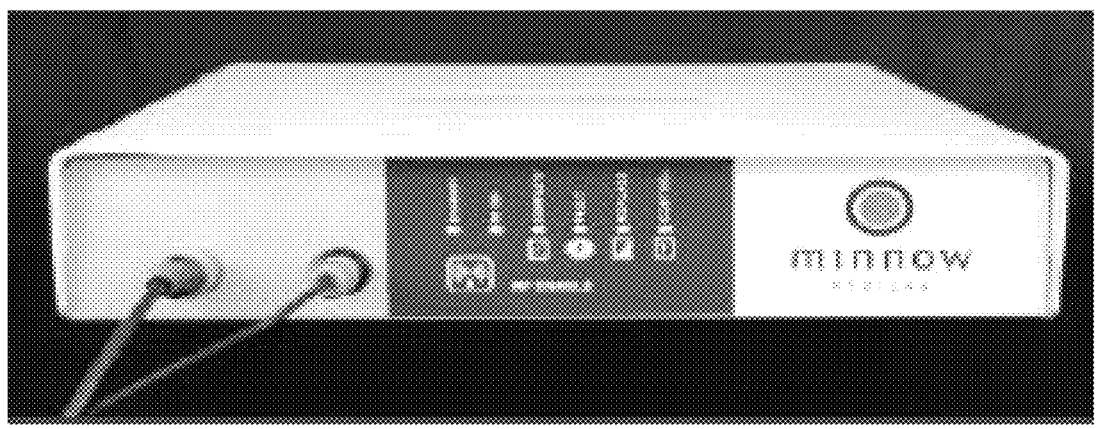

Referring now to FIG. 4A, an exemplary balloon catheter structure having an array of electrodes thereon can be seen. FIG. 4B illustrates an exemplary RF generator for energizing the electrodes of the balloon catheter of FIG. 4A. The balloon catheter and RF generator of FIGS. 4A and 4B were used in a series of experiments on animal models, with the balloons having diameter sizes ranging from about 3 mm to about 8 mm. The test subjects comprised Healthy domestic swine and Yucatan Mini-Swine. Atherosclerotic disease was induced (Injury & HFHC diet), to demonstrate the ability of a system including the balloon catheter and RF generator of FIGS. 4A and 4B to deliver controlled therapy to artery walls. Histology was obtained at post-treatment endpoints to determine the extent of tissue damage and the appropriate treatment dose ranges.

Electrodes 34 may be mounted on balloon 20 using any suitable attachment. In the embodiment shown in FIG. 5A, electrodes 34 are mounted or made on a flexible substrate or "flexible circuit" 35 that is attached to the balloon 20 with a suitable adhesive. The associated conductors 36 are attached to the catheter body 14. The flexible circuit 35 should be flexible to allow folding and inflation of the balloon. Each flexible circuit 35 includes multiple pads 34, for example, a preferred embodiment includes sixteen pads arranged in a linear array electrode.

Referring now to FIG. 5B, a flexible circuit panel 110 having flexible circuits 112, 114, and 116 is shown. Each of the flexible circuits include electrically conductive leads 118 that extend between proximal electrical contacts 120 and distal electrodes 122. Leads 118 are supported by a flexible polymer substrate 124, and the flexible circuits may be used in catheter 12 (see FIG. 1), for example, by cutting the substrate around and/or between the electrical components of the circuit, mounting the electrodes to balloon 20, and extending leads 118 toward and/or along catheter body 14 for electrical coupling to controller or processor 40 and energy source 42. One or more flexible circuits may be mounted to balloon 20, with the electrodes of each flexible circuit optionally providing a grouping or sub-array of electrodes for treating a plurality of remodeling zones in the target tissue. Alternative sub-arrays may be provided among electrodes of different flexible circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

Still referring to FIG. 5B, multiplexing between selected electrodes of an array or sub-array can be effected by selectively energizing electrode pairs, with the remodeling zones for the sub-array being disposed between the electrodes of the pairs so that the energy passes therethrough. For example, a pair of electrodes selected from electrodes 1, 2, 3, 4, 5, and 6 of flexible circuit 112 (with the selected electrodes optionally being positioned opposite each other) may be energized and then turned off, with another pair then being energized, and so forth. The firing order might be 1 and 4, then 2 and 5, then 3 and 6. Bipolar potentials between the electrodes of the pair can induce current paths in the same general tissue region, with the power dissipated into the tissue optionally remaining substantially constant. This provides a duty cycle of about ⅓ with respect to heat and/or losses at each electrode surface. The four electrode configurations of flexible circuits 114 and 116 could be used in a similar manner. Monopolar energy might also be applied using a larger ground pad on the skin of the patient or the like.

FIG. 5C shows flexible circuit panels 128 having flexible circuits 35 for use in FIG. 5A. Each of the flexible circuits 35 include electrically conductive leads 36 that extend between proximal electrical contacts 132 and distal electrodes 34. In the embodiment shown, each leg of flexible circuit 35 contains 16 electrodes 34 connected with one contact 132. This minimized the number of wires needed for conductive leads 36. The electrode pad may be 0.5 mm wide with 0.2 mm spacing between electrodes 34. The length and width of the electrode pad and number of electrodes may be changed for a desired impedance, for example, to match the impedance of the controller or generator. Leads 36 are supported by a flexible polymer substrate 134, and the flexible circuits may be used in catheter 12 (see FIG. 1), for example, by cutting the substrate around and/or between the electrical components of the circuit, mounting the electrodes to balloon 20, and extending leads 36 toward and/or along catheter body 14 for electrical coupling to controller or processor 40 and energy source 42. One or more flexible circuits may be mounted to balloon 20, with the electrodes of each flexible circuit optionally providing a grouping or sub-array of electrodes for treating a plurality of remodeling zones in the target tissue (See FIGS. 8A-8D). Alternative sub-arrays may be provided among electrodes of different flexible circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

In one embodiment, a solid insulated wire of suitable size is flattened on a distal end, for example being coined or rolled, squashing the wire to create a shape appropriate for an electrode 34. The insulation along the coined surface is removed. In some embodiments, the wire is made of platinum, while in other embodiments, the coined surface is electroplated with gold. The wire and electrode are then placed in the correct position and adhered to the balloon 20.

Figure 6A:
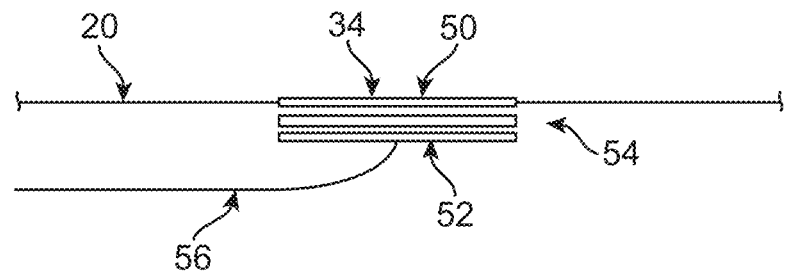
FIGS. 6A and 6B schematically illustrate one embodiment of electrodes having an electroplated balloon portion with an internal electrode base.
Figure 6B:
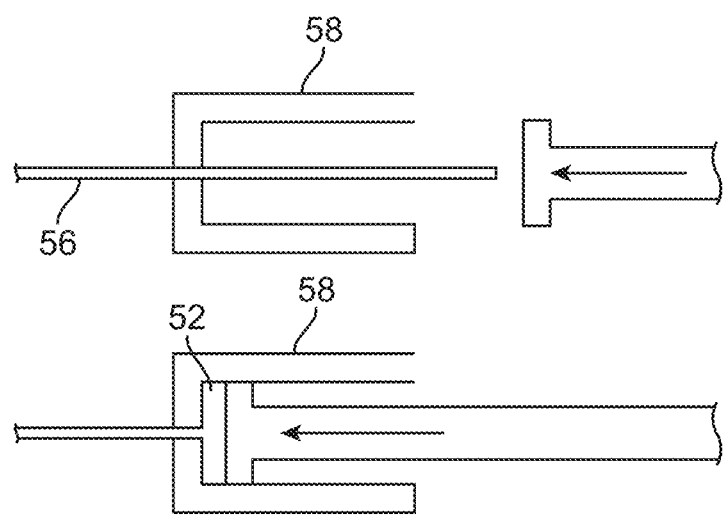

FIG. 6A shows one embodiment in which electroplated portions 50 of a balloon 20 act as the electrodes 34 with an electrode base 52 placed on the inside of the balloon 20. In this embodiment, a portion of a balloon is electroplated so it may conduct electricity through its wall. Electroless plating or metal deposition may also be used. The wire-electrode 52 is adhered to the inside of the balloon with conductive epoxy 54, the balloon becomes the surface of the electrode 34. To minimize the current density within the wall of the balloon, the wire electrode may be in the same pattern as that electroplated on the balloon. The wire-electrodes may be manufactured from a wire 56 in a forging process similar to that used in the making of nails, shown in FIG. 6B. An end of a magnetic wire 56 is placed into a forging mold 58 so that a length of wire whose volume is equal to that of the desired electrode is extended into the mold and forged into the electrode base 52. The wire-electrode, with the exception of the electrode base, may be insulated, so that the electrodes are isolated from one another and from the fluid used for balloon inflation. This method will encapsulate the assembly, minimize the risk of electrode delamination, increase the manufacturing yield, and is adaptable to any desirable electrode shape and patterning.

In another embodiment, electrodes 34 contain materials of differing specific resistivity cured on the balloon 20. One example is using an excimer laser to selectively cure photocurable ink on the balloon. Thus, electrode pads and traces may bye directly mounted on the balloon. This process starts by covering the balloon with photocurable or photoimageable conductive ink. A laser is then used to direct write the traces and electrode pads (UV cure) The uncured conductive ink is then removed or rinsed off. A cover layer is placed over the entire balloon and circuits, such as a parylene coating. The parylene coating is then removed to expose the electrode pads, for example, using an excimer laser. The electrode pads are then coated with a conductive material, such as Ni/Au. In another embodiment, a direct drive laser printer is used to lay down a conductive ink circuit with electrode pads and traces on the balloon surface.

In some embodiments, small holes may be used to perfuse a fluid on or near the electrodes to eliminate sticking of the electrodes to the artery tissue. The holes may be less than 1 μm in diameter and may be made with a laser or ion beam. The holes may be made in the electrodes, flexible circuit, and/or balloon. In one example, electrode pads on a flexible circuit are designed with vias that are plated. The flexible circuit is mounted on a balloon and a laser or ion beam is used to create the holes in the flexible substrate and balloon. There may be several holes in the flexible/balloon for every electrode pad. The balloon may then be perfused with standard perfusion balloon equipment or specialized equipment. The perfusion approach may also provide additional advantages beyond eliminating sticking, such as carrying away heat or regulating impedance of the load.

In some embodiments if may be advantageous to embed electrodes 34 into the artery tissue. The electrodes may have features to assist in imbedding, such as sharpened edges, needle protrusions, or the like, capable of piercing the artery tissue. For example, in a diseased tissue there will be some fibrous surface tissue surrounding the lumen that may tend to conduct energy, thereby avoiding the diseased tissue. This fibrous surface may tend to dominate any impedance measurement if they are probed superficially. By digging the electrodes into the wall of the fibrous cap, it may be possible to direct energy through the fibrous tissue directly into the diseased tissue, or closer to the diseased tissue. The energy may be Joule heating or a current source that puts more heating into the diseased tissue with higher resistively. The healthy tissue can dissipate the energy without significant damage. This technique may also assist in detecting diseased tissue electrically.

Monitoring the space between electrodes or electrode flexible circuits during inflation may assist in determining the direction of diseased tissue within an artery. The space between pairs of electrodes increases with pressure in an elastic balloon when it is unconstrained during inflation. When a balloon is placed within an eccentrically effected diseased tissue, the diseased portion stretches less than the healthy tissue. So the change in the distance between the pairs changes more in the healthy tissue and less in the diseased tissue, indicating the direction, and maybe the amount, of diseased tissue in the artery.

Monopolar Treatment

Figure 7A:
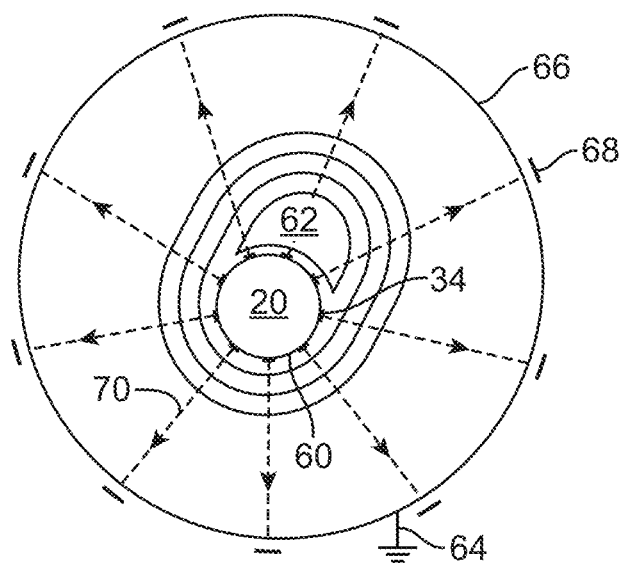
FIGS. 7A and 7B schematically illustrate one embodiment of balloon catheter system for use for monopolar energy treatment.

FIG. 7A shows one embodiment of balloon catheter system for use for monopolar treatment of diseased tissue in a leg. A balloon catheter 20 having electrodes 34 are positioned within an artery lumen 60 having diseased tissue 62. An electrical ground 64 is positioned on the patients skin, or may be many ground electrode pads 68 positioned around a patients leg 66, such a in a band or sock. When power is applied to the multiple monopolar electrodes 34 arranged around the circumference of the artery lumen, energy 70 is directed radially outward through the artery wall.

By driving energy 70 radially outward, it is possible to force energy through the disease tissue 62, which has a higher electrical resistivity than healthy tissue. By applying low power for a long time duration, the disease tissue may be treated. Low power is defined as the level of power which healthy tissue can dissipate the heat in a steady state without the healthy tissue temperature rising above a given threshold. The temperature may be between 45° C. and 50° C., which will denature the actin and myosin proteins that enable elastic recoil, without causing excessive necrosis. The energy may be applied for a long time, where long is defined by the desired duration of the procedure, bounded on the high side by the amount of time healthy tissue can withstand the elevated temperature being caused, and bounded on the low side by the amount of time the diseased tissue needs for treatment to be complete. By treating for a long time, it is possible to accumulate heat in the diseased tissue, which has a lower heat capacity per mass and a lower thermal conductivity. Variability in impedance can be compensated by the controller, in order to apply either constant power, constant current, or constant voltage, whichever has the most advantage.

Figure 7B:
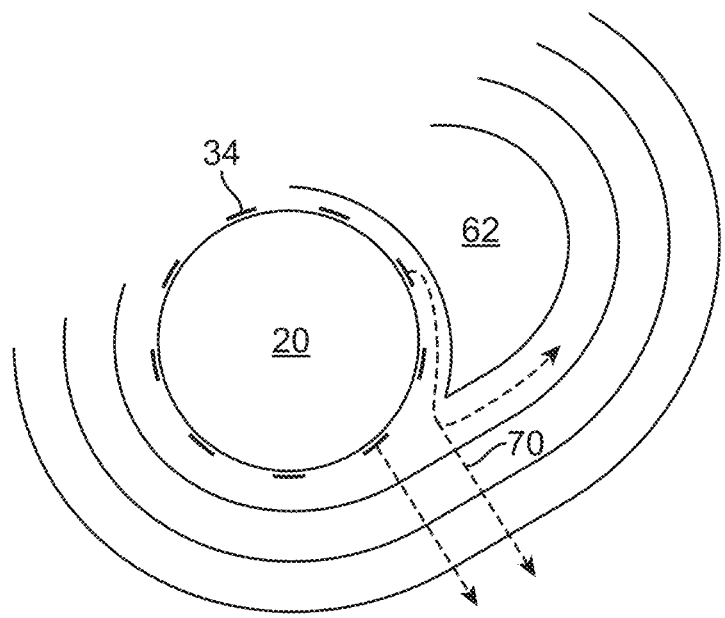

The energy in the monopolar treatment shown if FIG. 7A travels outwardly from the electrodes 34 and treats both diseased 62 and healthy artery tissue. Looking at the current path in tissue, diseased artery tissue, such as fat or lipidic material, has a low electrical conductivity compared to other artery constituents. If this is true, the current 70 may go around the diseased tissue 62 if possible, and find a less restrictive path, such as shown in FIG. 7B.

In some embodiments, internal 34 and external electrodes 68 may be used to map artery plaque. By assembling a matrix of impedance readings, both bipolar and monopolar, it may be possible to map the constituent composition and location of the disease in the artery. Once this information in known, it may be possible to treat using the same known electrode positions. The treatment can either by monopolar or bipolar. Analysis is done weighting the contributions of the distance between the internal and external electrodes with the contribution differences in cellular composition in each path. Design of the external electrodes 68 may be guided by computational capacity, maximizing the number of electrode points both around the circumference and along the patients leg (lengthwise). In one embodiment, the external electrodes 68 are embedded in a sock or sleeve forming a matrix of electrodes on the outside of the patients skin. This may device gives improved resolution in measuring current paths from multiple directions and provides a way to identify what the internal electrodes are opposed to in the artery.

Bipolar Treatment

Figure 8A:
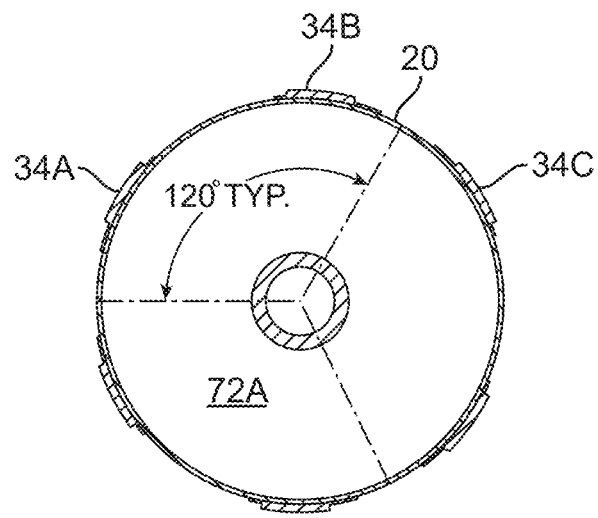
FIGS. 8A-8D schematically illustrate placement of electrode pairs for use in bipolar energy treatment.
Figure 8B:
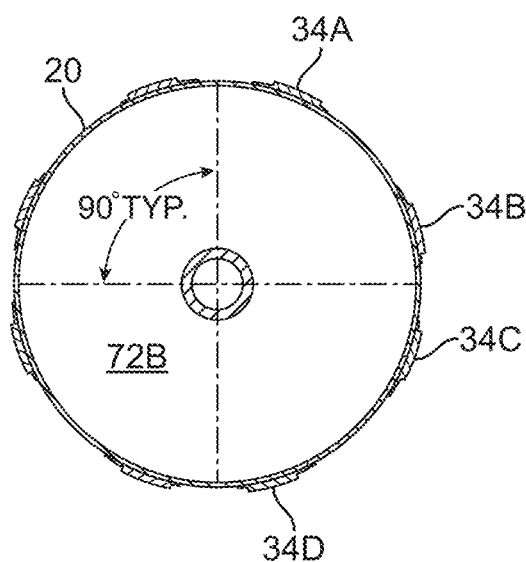
Figure 8C:
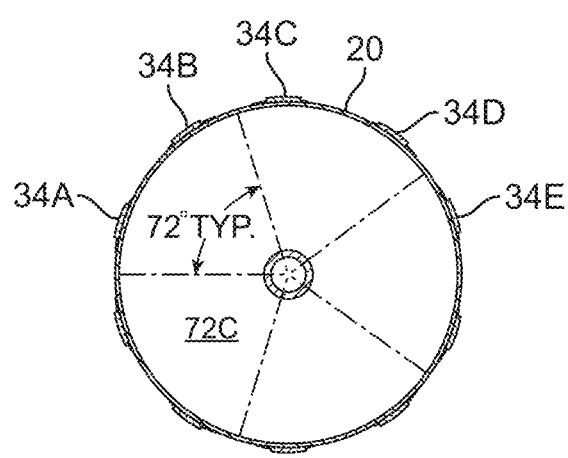
Figure 8D:
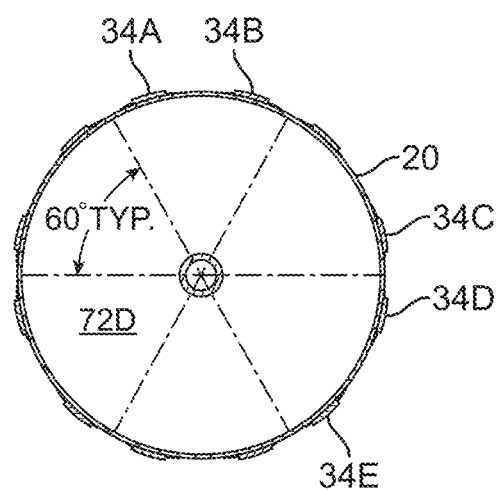

FIGS. 8A-8D show different embodiments of electrodes 34 mounted circumferentially on balloon 20 to provide treatment to artery tissue using bipolar energy between electrode pairs 34A and 34B. The electrode pairs may be any electrode pairs on the balloon, for example, in some embodiments, the electrode pairs may be 34A and 34C, or 34A and 34D, or 34A and 34E, or any combination of 34A-34E. This arrangement creates an energy path through the tissue that delivers heat or energy in particular treatment zones or segments 72 to the artery tissue between the electrode pairs ("remodeling zones"). Using different combinations of electrode pairs may reduce or eliminate gaps between the remodeling zones by using overlapping pairs. Using electrode pairs with bipolar energy may avoid some potential issues of the monopolar approach. Diseased artery tissue has a higher electrical resistively than healthy artery tissue. If all the electrodes are energized, such as in a monopolar system, the heat or energy may flow through the healthy artery tissue and not into the diseased artery tissue (see FIG. 7B). By using pairs of electrodes in a bipolar system, the heat or energy will go through the healthy tissue, diseased tissue, or a combination of both healthy and diseased tissues between the electrode pairs in the remodeling zones. Any number of electrode pairs may be used in different patterns or arrays. In the embodiments shown, the pitch between electrode pairs remains the same, for example 3.14 mm, so that the treatment volume is the same regardless of balloon size and each of the electrode pairs use the same energy. As the balloons become larger, more electrode pairs are placed on the balloon, such as shown in FIGS. 8A-8D. The spacing between electrode pairs may range from about 0.25 to 2.5 mm, depending on balloon size. The maximum distance (angle) between electrode pairs is 180 degrees on the balloon. FIG. 8A shows a balloon having a 3.0 mm diameter with three electrode pair in three segments 72A. FIG. 8B shows a balloon having a 4.0 mm diameter with four electrode pair in four segments 72B. FIG. 8C shows a balloon having a 5.0 mm diameter with five electrode pair in five segments 72C. FIG. 8D shows a balloon having a 6.0 mm diameter with six electrode pair in six segments 72D.

Figure 9A:
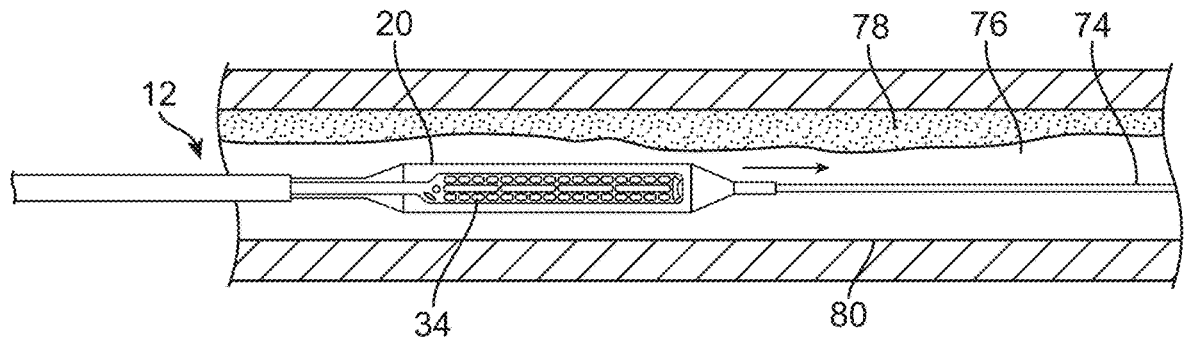
FIGS. 9A-9C illustrate a method of using a balloon catheter system treating artery tissue.
Figure 9B:
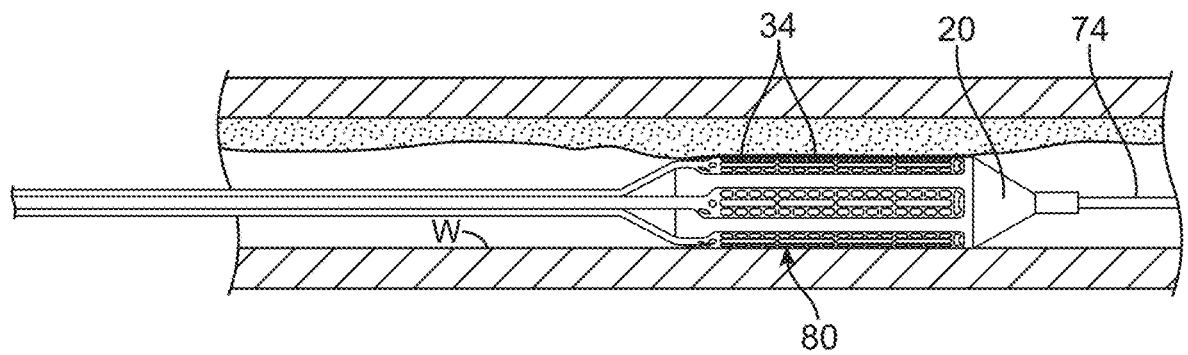
Figure 9C:
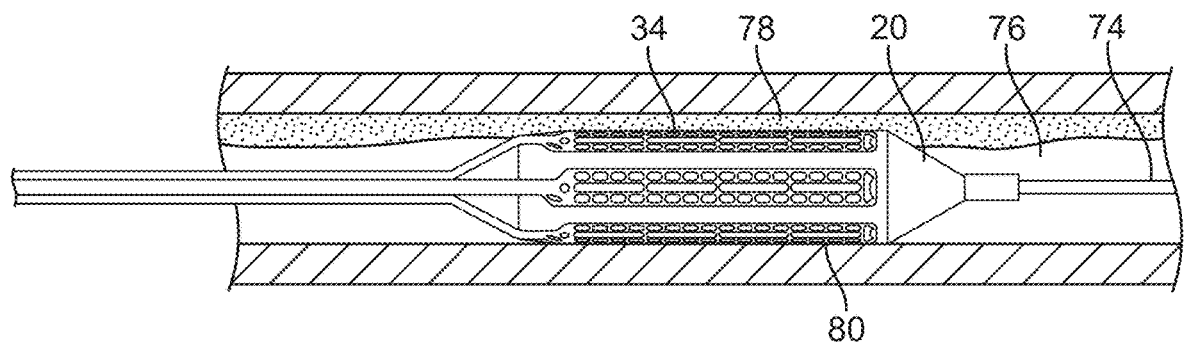

The use of catheter system 10 for remodeling artery tissue by heating can be understood with reference to FIGS. 9A-9C. As seen in FIG. 9A, accessing of a treatment site will often involve advancing a guidewire 74 within a blood vessel 76 at a target region of diseased tissue, such as atherosclerotic material 78. Location of balloon 20 may be facilitated by radiopaque markers or by radiopaque structure (or corresponding radiopaque markers placed on or near) balloon 20, and/or by the use of radiopaque electrodes 34. A wide variety of guidewires may be used. For accessing a vessel having a total occlusion, guidewire 74 may comprise any commercially available guidewire suitable for crossing such a total occlusion, including the Safe-Cross™ RF system guidewire having forward-looking optical coherence reflectometry and RF ablation. Where atherosclerotic material does not result in total occlusion of the lumen, such capabilities need not be provided in guidewire 74, although other advantageous features may be provided. Guidewire 74 may be positioned under fluoroscopic (or other) imaging.

Catheter 12 is advanced distally over guidewire 74 and positioned adjacent to atherosclerotic material 62. Balloon 20 expands radially within the lumen of the blood vessel so that electrodes 34 radially engage atherosclerotic material 78. As atherosclerotic material 78 may be distributed eccentrically about catheter 12, some of electrodes 34 may engage both atherosclerotic material 78 and healthy tissue 80, as can be understood with reference to FIGS. 9B and 9C.

In some cases, an imaging may be used for identification and/or characterization of atherosclerotic materials, plaques, tissues, lesions, and the like from within a blood vessel. Suitable imaging catheters for use in the present catheter system are commercially available from a wide variety of manufacturers. Suitable technology and/or catheters may, for example, be commercially available from SciMed Life Systems and Jomed-Volcano Therapeutics (providers of intravascular ultrasound catheters), Light Lab™ Imaging (developing and commercializing optical coherence tomography catheters for intravascular imaging), Medtronic CardioRhythm, and the like. Still further alternative technologies may be used, including ultra fast magnetic resonance imaging (MRD, electrical impedance atheroma depth measurements, optical coherence reflectometry, and the like. Non-invasive imaging modalities which may be employed include X-ray or fluoroscopy systems, MRI systems, external ultrasound transducers, and the like. Optionally, external and/or intravascular atherosclerotic material detectors may also be used to provide temperature information. For example, a system having an MRI antenna may detect tissue temperatures such that a graphical indication of treatment penetration may be presented on the system display. Tissue temperature information may also be available from ultrasound and/or optical coherence tomography systems, and the temperature information may be used as feedback for directing ongoing treatments, for selecting tissues for treatment (for example, by identifying a hot or vulnerable plaque), and the like.

As discussed above, electrodes 34 are positioned circumferentially around the balloon 20. RF energy is directed to electrodes adjacent pairs of electrodes 34A and 34B, treating both atherosclerotic material 78 and the healthy tissue 80. The controller 40 may energize the electrodes with about 0.25 to 5 Watts average power for 1 to 180 seconds, or with about 4 to 45 Joules. Higher energy treatments are done at lower powers and longer durations, such as 0.5 Watts for 90 seconds or 0.25 Watts for 180 seconds. Most treatments in the 2 to 4 Watt range are performed in 1 to 4 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel. The mechanisms of ablating atherosclerotic material within a blood vessel have been well described, including by Slager et al. in an article entitled, "*Vaporization of Atherosclerotic Plaque by Spark Erosion*" in J. of Amer. Cardiol. (June, 1985), on pp. 1382-6; and by Stephen M. Fry in "*Thermal and Disruptive Angioplasty: a Physician's Guide*;" Strategic Business Development, Inc., (1990) the full disclosures of which are incorporated herein by reference.

Referring now to FIG. 7C, as described above, balloon 20 may be an angioplasty balloon that combines heating with opening the artery lumen. In some embodiments, injury caused to the atherosclerotic material with the energized electrodes or other energy directing surfaces may result in subsequent resorption of the injured tissue lesions so as to provide further opening of the vessel after termination of treatment as part of the healing process.

In some embodiments, balloon 20 may be repeatedly contracted, axial movement of the catheter 12 employed to reposition balloon 20, with subsequent expansion of balloon 20 at each of a plurality of treatment locations along atherosclerotic material 78.

The exemplary catheter devices and methods for their use described herein are intended for application in the lumen of vessels of the human anatomy. The anatomical structure into which the catheter is placed may be, for example, the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Figure 10:
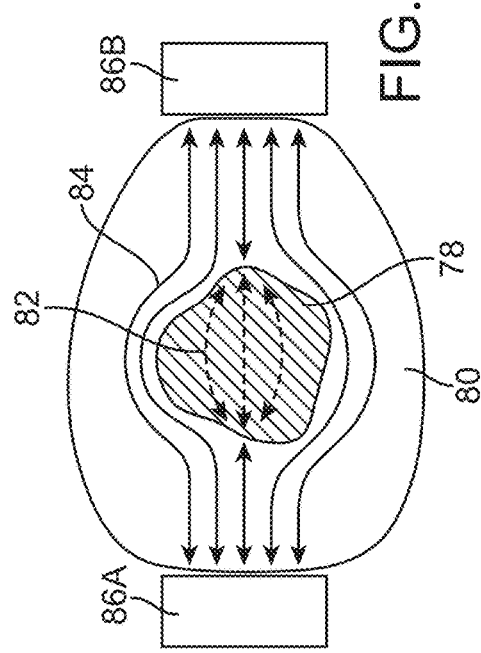
FIG. 10 illustrates frequency targeting of tissues.

Frequency targeting of tissues is illustrated in FIG. 10. Different tissue types have different characteristic electrical impedances that cause the tissue to absorb energy of certain frequencies or frequency ranges more readily than others. By applying energy at the specific frequency or range of frequencies that the tissue is more conductive, energy penetrates the tissue more readily. In general, it has been shown that samples of diseased tissue exhibit higher impedance characteristics than samples of healthy tissue. In the case where a diseased area of tissue 78 is surrounded by relatively healthy tissue 80, the healthy tissue is likely to shield the diseased tissue from electrical current flow due to the lower impedance of the healthy tissue. Hence, minimal (or less than the desired) current flow 82 may pass through diseased tissue 78, and heavier current flow 84 may be seen in low impedance healthy tissue 80 when bipolar current is transmitted between electrodes 34A and 34B. Typically, the frequency ranges in which tissue impedance varies to a useful degree occur between 30 kilohertz and 30 Megahertz.

Frequency targeting seeks to deliver more energy to the diseased tissue by determining the frequency or range of frequencies at which the impedance of the diseased tissue is equal to or less than that of the healthy tissue, such as by operation at or above a threshold frequency. Energy delivered at the specified frequency or range of frequencies will cause more heat to be dissipated in the diseased tissue than energy delivered outside of those specific frequencies.

Figure 11:
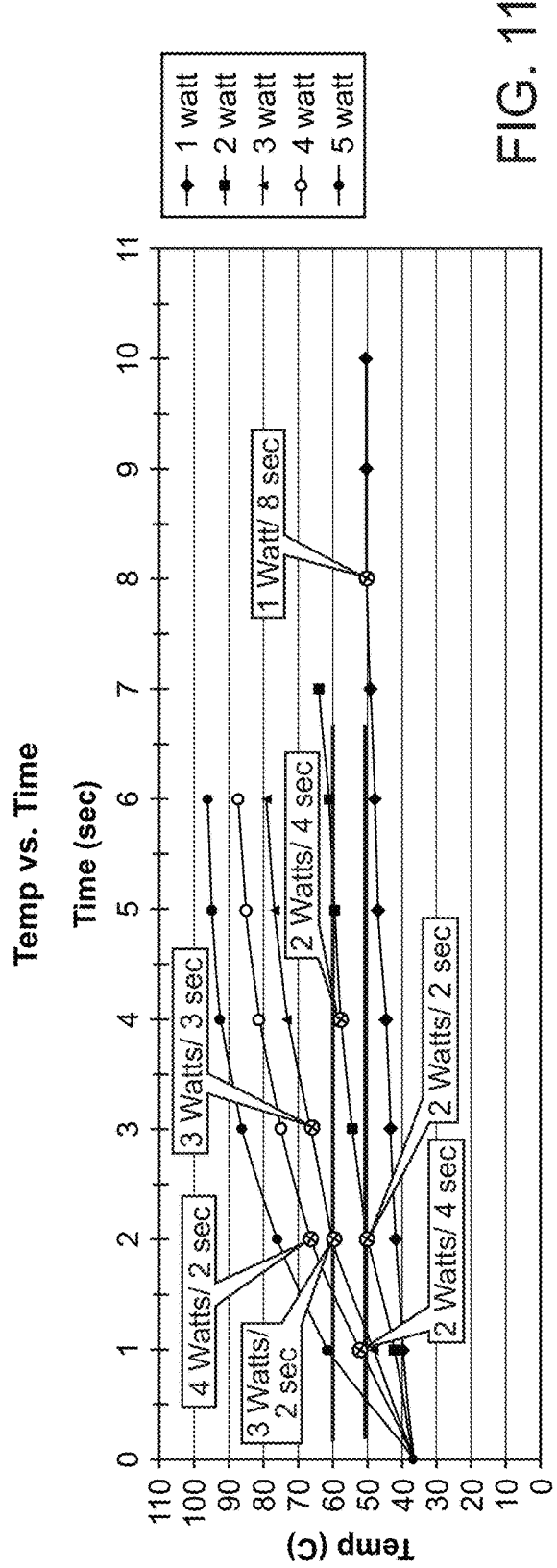
FIG. 11 illustrates various electrode energy settings to achieve temperatures between 50° C. and 65° C.

FIG. 11 shows some results of testing done on a cadaver aorta. By using an average power between 1 and 5 Watts for between 0.5 and 10 seconds the surface temperature reached was between 50 and 65° C. Sample doses are shown below in Table 1

TABLE 1

| Power | Time | Temp |
|---|---|---|
| 1 Watt | 8 sec | 50° C. |
| 2 Watts | 2 sec | 50° C. |
| 3 Watts | 1.3 sec | 50° C. |
| 4 Watts | 1 sec | 50° C. |
| 5 Watts | .5 sec | 50° C. |
| 2 Watts | 4 sec | 60° C. |
| 3 Watts | 2 sec | 60° C. |
| 4 Watts | 1.5 sec | 60° C. |
| 5 Watts | 1 sec | 60° C. |
| 3 Watts | 3 sec | 65° C. |
| 4 Watts | 2 sec | 65° C. |

As the energies and powers for characterizing and/or treating tissues are relatively low, the power source may optionally make use of energy stored in a battery, with the power source and/or associated controller optionally being contained within a hand-held housing. Use of such battery-powered systems may have benefits within crowded operating rooms, and may also help avoid inadvertent over treatment. The batteries may be disposable structures suitable to be included in a kit with a single-use catheter, while the processor circuitry may be re-useable. In other embodiments, the batteries may be rechargeable.

Electrode Design Considerations

Delivering RF energy directly to a specimen requires a conductive path to be formed between two terminals or poles of an energy source. Currently there are two polar configurations that exist which satisfy this condition: a mono-polar configuration (FIG. 12A) and a bipolar configuration (FIG. 12B). In a mono-polar configuration there is a single pole or electrode from which the energy emanates and a grounding plate or pad to absorb the energy and complete the circuit. This configuration creates higher energy densities at the electrode than at the grounding pad which results in a single effected area or treatment zone at the electrode which is directly related to the geometry of the electrode and the power applied to the electrode. As the surface area of the mono-polar electrode increases, so does the size of the treatment zone. The bi-polar configuration, on the other hand uses two poles or electrodes to set up an electric field between the electrodes thus creating a conduction path for the current to flow. Unlike the mono-polar electrode configuration where only one geometric entity, surface area is deterministic to the treatment zone, the bi-polar electrode configuration has three, electrode separation, parallel length and width, each of which have a separate and distinct effect on the treatment zone.

If we take into consideration the effect each geometric entity has on the effected treatment zone and the overall impedance as seen by the generator, we find that the separation or distance between electrodes has the greatest effect, followed by parallel length and lastly electrode width. Electrode separation is governed by Coulombs law which states that the force between two charged objects is inversely proportional to the square of the distance between them. In other words at very close distances the impedance as seen by a generator is very small and as we separate the electrodes the impedance increases at a rate that is proportional to the square of their separation. As this separation increases, a higher potential energy is generated due to the increase in impedance creating a greater flux density which results in a greater treatment depth. The effect of increasing the parallel length shared by the two electrodes causes the treatment zone to increase only as much as the parallel electrode length is increased. There are no additional depth effects only an increase due to added length. This additional length causes the impedance as seen by the generator to decrease due to the increase in potential parallel paths for the current to flow through. Electrode width has the least effect on the treatment zone and is governed by the same laws as electrode separation. As the width of the electrode is increased incrementally, the added effect is small due to the inverse square law for each incremental element placed on the outer edges of the existing electrode elements. Although this effect may be small it aides in reducing the surface heat generated by reducing the current density at the inside edge of the electrode pairs. This effect is amplified as the conductance of the electrode material approaches the conductance of the tissue being treated due to the path of least resistance becoming the tissue rather than the electrode itself.

In order to better control the flow of electrical current to the inside of the arterial wall and to have a therapy which has the capability to selectively treat a desired area of an artery, the bipolar configuration is clearly the most desirable method of implementation.

Implementation requires that the electrodes be in contact with the inner surface of the arterial wall so the conductive path is the artery itself and not the more conductive blood flowing within the artery. Many mechanism may be used to contact the electrodes to the inner surface of the arterial wall. In the present case, a balloon is used as the deployment mechanism. The bipolar electrodes may be arranged on the balloon either a radial topology (FIG. 13) or a longitudinal topology (FIG. 14).

Each topology, radial and longitudinal, provides for a bi-polar configuration as well as offer a selective therapy, however the method of selectivity of each topology differ. The radial topology offers longitudinal selectivity along the length of an artery while the longitudinal topology offers circumferential selectivity. When we then take into consideration how atherosclerosis forms within an artery, we find that it starts out at a localized area on the arterial wall and spreads along the wall sometimes completely occluding the flow of blood. In the case of complete occlusion or stenosis where the diseased tissue is concentric about the entire circumference of the artery (FIG. 15A), each topology will suffice. However, in the case where the diseased tissue is eccentric and a portion of the artery is still healthy tissue (FIG. 15B), the longitudinal topology is preferred due to the difference in thermal and electrical conductivity between the healthy tissue and diseased tissue. This difference, in the case of the radial topology will cause the healthy portion to be treated more than the disease which is not a desirable outcome. When we also take into consideration that the balloon must first be folded to reduce the cross sectional area for deployment, it becomes clear that the longitudinal topology appears to be the better choice.

The next was how to arrange the electrode on the balloon. How long should the electrodes be? How wide should the electrodes be? And how far apart should the electrodes be separated? An initial starting point was to use four balloon diameters, 3 mm, 4 mm, 5 mm and 6 mm. An electrode geometry configuration was designed so that each balloon diameter would be capable of accepting the same electrode geometry configurations, so no matter what size balloon was being used, the treatment could be the same. With this configuration, the basic relationship of the circumference of the balloon is related to the diameter by the factor of $\pi$ (pi). The circumference of the balloon is equal to its diameter multiplied by $\pi$ (pi). Using the balloon diameters to dictate the number of electrode pairs placed on a balloon, the center to center electrode spacing would be $\pi$ (pi) divided by 2. This configuration allows for the even distribution of electrodes about the circumference of the balloon for each whole number balloon diameter. With the electrodes center to center spacing decided, next is to figure out the ratio of the electrodes width to their separation. This ratio would have to take in to consideration the desired depth of treatment, as well as the effects of surface heating. Taking these factors into consideration, a ratio of approximately 1:2 was selected. The actual numbers used were an electrode width of 0.5 mm with a spacing of 1.07 mm, which fits nicely with the $\pi/2$ center to center separation. This selected configuration also allowed twice the number of possible treatment zones for each balloon diameter (2$n$) as compared to one electrode pair for each millimeter of balloon diameter. Having twice the number of available treatment zones also meant that there was a greater potential for selectivity.

The last geometric entity yet to be decided was the length of the electrodes. When trying to measure the impedance of the tissue the electrodes are in contact with, it is more desirable to implement shorter electrodes so there is more sensitivity in the measurement and also more immunity to noise. Shorter electrodes on the other hand also mean that to treat an adequate area there needs to be many more electrode pairs and as a result more wires connecting those electrodes to the generator which will ultimately decrease the flexibility and complexity of the catheter. If long electrodes are used to reduce the wire count and to increase the potential treatment area, a different set of problems arise. Although long electrodes allow for a potentially larger treatment zone, they also allow for the possibility of overlapping into a healthy area which would result in an uneven treatment which could preferentially treat the healthy area rather than the diseased. The other disadvantage is the reduced sensitivity when measuring impedance due to the increase in available current paths which also results in the need for larger diameter wires to accommodate the increased current requirements. In solving this problem available balloon lengths were looked at and 16 mm electrodes were chosen to use on a 20 mm balloon. This selection allowed for reasonable sensitivity while keeping the wire size to a minimum.

There are many available methods for placing electrodes onto a balloon, ranging from vapor deposition to flexible circuitry to individual machined electrode and flattened wire. The main consideration was a proven manufacturing method, materials that could be placed in the body and parts that could be handled fairly easily without damage. Taking these factors into consideration, the use of flexible circuitry was chosen as the method to manufacture the electrodes. Flexible circuitry met all of the above criteria while still being flexible after being mounted to the balloon. When designing the flexible electrodes, the design should ensure that the electrodes are in firm contact with the arterial wall, evacuating as much of the blood as possible. To achieve this, individual rounded pads were selected that were 0.5 mm wide by 0.8 mm long separated by a distance of 0.2 mm. Pads were connected together in "string" using 0.5 oz Cu traces with 0.5 mil polyimide on the front and back and between electrode pads providing insulation and isolation. The pads were then plated up so the finished pad height was above polyimide cover-lay. The 0.2 mm separation between connected pads was implemented to retain flexibility and to ensure the connection was maintained during flexing. An electroless nickel-immersion gold coating was used to cover all exposed copper for safety. These electrodes were then adhered to the balloon using a flexible UV cured adhesive.

Figure 16:
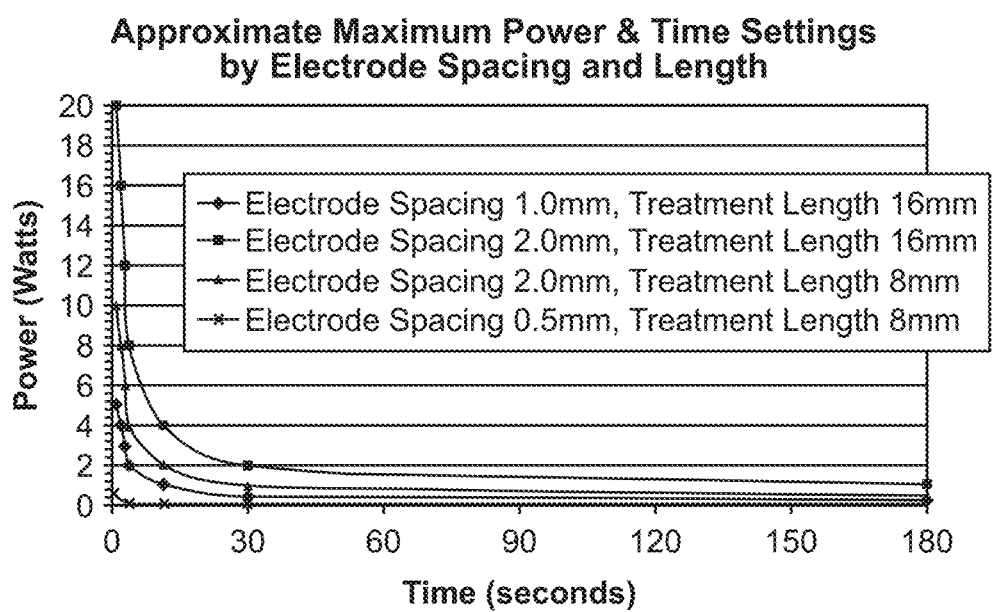
FIG. 16 graphically illustrates advantageous treatment power and time ranges for different electrode geometries, for use in embodiments of the invention.

Referring now to FIG. 16, suitable power ranges for providing the desired heating of the target tissue, and/or for limiting of heating to collateral tissues, may depend at least in part on the time for which energy is applied, on the electrode (or other energy transmitting surface) geometry, and the like. First, when applying the treatments described herein to tissues with electrodes, there may be preferred a load impedance range of the tissues within the circuit so as to avoid having to apply voltages and/or currents that are outside desirable ranges, particularly when applying powers within ranges described herein. Suitable load impedance ranges would generally be within a range from about 20 Ohms to about 4500 Ohms, more typically being in a range from about 40 Ohms to about 2250 Ohms, and preferably being in a range from about 50 to about 1000 Ohms.

The load impedance of the tissue within the circuit may depend on the characteristics of the tissue, and also (for example) on the geometry of a bipolar pair of electrodes that engage the tissue, as the electrodes geometries influence the geometry of the tissue effectively included within the circuit. The tissue to which energy is directed may have a specific conductivity in a range from about 0.2 Siemens per meter to about 0.5 Siemens per meter. Different types of diseased tissues may have specific conductivities in different ranges, with some types of diseased tissues having specific conductivities in a range from about 0.2 Siemens per meter to about 0.35 Siemens per meter, while others fall within a range from about 0.35 Siemens per to about 0.5 Siemens per meter. The spacing between the pair of electrodes and the length of electrodes (transverse to their spacing) will both have effects on the load impedance, with most embodiments having electrode pair spacings (adjacent edge-to-edge) of between 0.25 mm and 2.50 mm, exemplary embodiments having electrode pair spacing of between 0.50 and 2.00 mm, and preferred embodiments having electrode pair spacing of between 0.75 and 1.50 mm.

Regarding the length and spacing of the electrodes within a particular pair, these factors are inter-related with the power and impedance. As the length of the electrodes decreases, the impedance seen by the generator will go up, but the volume of tissue will go down, so that the power setting on the generator may be decreased. As the gap between the electrodes widens, the impedance seen by the generator will also go up, but the volume of tissue will go up as well, so that the power setting on the generator should be increased. Hence, there are roughly opposed effects on load impedance when you decrease electrode length and electrode spacing.

Desired power, energy, and time of the treatment are likewise inter-related, and may also be at least related with electrode geometry. Speaking very generally, lower power treatments applied for long times tends to result in treatments with relatively higher total energies, while higher power treatments for shorter times tends to result in lower energy treatments. More specifically, at relatively low average power (1 W or less) the total energy delivery per treatment may range from 8 to 45 Joules. At higher power (more than 1 W), the total energy delivery per treatment may range from 4 to 15 Joules. If the electrode spacing were doubled, power may increase by four times. The power 180 seconds are covered as well. Alternative suitable treatment range falls within or near the set of curves shown in FIG. 16, which shows approximate numbers for maximum power and time by electrode dimensions. Still further alternative treatment parameter values can be understood with reference to Table 2, which shows total energies for different combinations of power and time for a few different electrode pair geometries.

TABLE 2

| Exemplary Peripheral Treatment Catheter | | | Alternative I Peripheral Treatment Catheter | | | Alternative II Peripheral Treatment Catheter | | | Exemplary Coronary Treatment Catheter | | |
|---|---|---|---|---|---|---|---|---|---|---|---|
| X = 1 mm, L = 16 mm | | Total | X = 2 mm, L = 16 mm | | Total | X = 2 mm, L = 8 mm | | Total | X = 0.5 mm, L = 8 mm | | Total |
| Time (s) | Power (W) | Energy (J) | Time (s) | Power (W) | Energy (J) | Time (s) | Power (W) | Energy (J) | Time (s) | Power (W) | Energy (J) |
| 1 | 5 | 5 | 1 | 20 | 20 | 1 | 10 | 10 | 1 | 0.625 | 0.625 |
| 2 | 4 | 8 | 2 | 16 | 32 | 2 | 8 | 16 | 2 | 0.5 | 1 |
| 3 | 3 | 9 | 3 | 12 | 36 | 3 | 6 | 18 | 3 | 0.375 | 1.125 |
| 4 | 2 | 8 | 4 | 8 | 32 | 4 | 4 | 16 | 4 | 0.25 | 1 |
| 12 | 1 | 12 | 12 | 4 | 48 | 12 | 2 | 24 | 12 | 0.125 | 1.5 |
| 30 | 0.5 | 15 | 30 | 2 | 60 | 30 | 1 | 30 | 30 | 0.0625 | 1.875 |
| 180 | 0.25 | 45 | 180 | 1 | 180 | 180 | 0.5 | 90 | 180 | 0.03125 | 5.625 | transmitted into the tissue can be calibrated and scaled to the particular electrode configuration, often in order to keep the power and energy density in a desirable range. Exemplary power ranges may be, for example from about 1 to 5 Watts. The duration is longer for the lower power settings, and typically varies from about 1 to 8 seconds. Very low power settings less than 1 Watt are also possible, using durations much longer than 10 seconds.

It is also possible to scale the power settings significantly by varying the electrode configuration. If, for instance, the inner edge-to-edge spacing of the electrodes are increased, roughly 4 times the power may be applied because the volume of tissue becomes roughly 4 times larger. As such, an electrode configuration that is somewhat different from the exemplary embodiments described herein could be used within a power range of roughly 4 to 20 Watts. Shortening the electrodes, and thus shortening and reducing the volume of the remodeling zones, would also affect the magnitude of the power that is appropriate to apply to the tissue volume.

Referring still to FIG. 16, in order to quantify this complex set of relationships, and bound the space within which the exemplary treatment device can operate, an empirical relationship between safe values of several of these parameters may be generated and provided graphically, in table form, or by a mathematical relationships. An exemplary equation describing a particularly advantageous relationship is:

$$\text{power} = b \cdot x^2 \cdot L \cdot (t^{(-0.59)})$$

where b is a parameter in the range of 0.2 to 0.6, x is the inner edge-to-edge spacing of the electrodes in millimeters, L is the length of the electrodes in millimeters (and also the approximate length of the remodeling zone), the power is in Watts, and t is time in seconds. b has units of Watts/(mm^3) *(seconds^0.59). Exemplary treatments in the range described by this equation includes treatments such as 4 Watts for 2 seconds, 3 Watts for 3 seconds, 2 Watts for 4 seconds, and 1 Watt for 12 seconds with the exemplary electrode geometries described herein. Additionally, very low power long duration treatments such as 0.25 Watts for While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A system, comprising:
   a catheter body having a proximal end and a distal end with an axis therebetween;
   a balloon supported by the distal end of the catheter body, the balloon having a low profile insertion configuration and a larger profile configuration;
   a plurality of flex circuits attached to the balloon and defining a plurality of remodeling zones that extend about a circumference of a body lumen when the balloon is in the larger profile configuration, each flex circuit comprising a pair of electrodes on a flexible substrate, the flexible circuits being sufficiently flexible to allow folding and inflation of the balloon; and
   a power source configured to electrically couple with the electrodes of the flex circuits, and to transmit a tissue remodeling energy between the electrodes of the pairs,
   wherein the power source is further configured to transmit the tissue remodeling energy to each of the plurality of remodeling zones such that the tissue remodeling energy transmitted to remodeling zones including both a target tissue and a collateral tissue heats the target tissue sufficiently to efficaciously alter the target tissue without causing thermal damage to the collateral tissue;
   wherein each of the flexible circuits includes an associated bipolar electrode pair;
   wherein the bipolar electrode pairs are configured to be energized with RF energy;
   wherein the bipolar electrode pairs have adjacent edge-to-edge spacings of between 0.25 mm and 2.50 mm; and
   wherein the bipolar electrode pairs are configured to provide a load impedance of from 20 to 4500 Ohms when delivering tissue remodeling energy to the target tissues.

2. The system of claim 1, wherein the power source is configured to energize the pairs of electrodes with about 0.25 to 20 Watts average power for a duration between 1 to 180 seconds or wherein the power source s configured to energize the pairs of electrodes so as to deliver 8 to 45 Joules of energy in a treatment.

3. The system of claim 1, wherein the system is configured to affect controlled delivery of the tissue remodeling energy using a characteristic of the target tissue measured with one or more of the pairs of electrodes or wherein the power source is configured to energize the pairs of electrodes so as to deliver 8 to 45 Joules of energy in a treatment.

4. The system of claim 3, wherein the characteristic comprises a load impedance.

5. The system of claim 1, wherein the target tissue has a specific conductivity within a range from 0.2 to 0.5 Siemens per meter.

\* \* \* \* \*